US006379881B1

United States Patent
Fouchier et al.

(10) Patent No.: US 6,379,881 B1
(45) Date of Patent: *Apr. 30, 2002

(54) NUCLEIC ACIDS AND METHODS FOR THE DISCRIMINATION BETWEEN SYNCYTIUM INDUCING AND NON SYNCYTIUM INDUCING VARIANTS OF THE HUMAN IMMUNODEFICIENCY VIRUS

(75) Inventors: Ronaldus Adrianus Fouchier; Johanna Schuitemaker, both of Amsterdam (NL)

(73) Assignee: Akzo Nobel, N.V. (NL)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/722,015
(22) PCT Filed: Apr. 19, 1996
(86) PCT No.: PCT/NL95/00142
    § 371 Date: Nov. 19, 1996
    § 102(e) Date: Nov. 19, 1996
(87) PCT Pub. No.: WO95/28500
    PCT Pub. Date: Oct. 26, 1995

(30) Foreign Application Priority Data

Apr. 19, 1994 (EP) .............................. 94201076

(51) Int. Cl.[7] ................................. C12Q 1/70
(52) U.S. Cl. ................ 435/2; 435/6; 536/23.72; 536/24.3; 536/24.33
(58) Field of Search ............... 435/5, 91.1, 91.33, 435/91.51, 6; 536/23.72, 24.3, 24.33

(56) References Cited

U.S. PATENT DOCUMENTS 5,468,613 A * 11/1995 Erlich et al. .................... 435/6
5,604,099 A *  2/1997 Erlich et al. .................... 435/6

OTHER PUBLICATIONS

Groenink et al., 1993, "Relation of Phenotype Evolution of HIV-1 to Envelope V2 Configuration," Science 260:1513–1516.*

DE Jong et al., 1992, "Human Immunodeficiency Virus Type 1 Clones Chimeric for the Envelope V3 Domain Differ in Syncytium Formation and Replication Capacity," J. Virol. 66(2):757–765.*

Kuiken et al., 1992, "Evolution of the V3 Envelope Domain in Proviral Sequences and Isolates of Human Immunodeficiency Virus Type 1 during Transition of the Viral Biological Phenotype," J. Virol. 66(7):4622–4627.*

Lewin, R., 1987, "When Does Homology Mean Something Else?" Science 237:1570.*

Reeck et al., 1987, ""Homology" in Proteins and Nucleic Acids: A Terminology Muddle and a Way out of it," Cell 50:667.*

(List continued on next page.)

Primary Examiner—Laurie Scheiner
Assistant Examiner—Jeffrey S. Parkin
(74) Attorney, Agent, or Firm—Myers Bigel Sibley & Sajovec

(57) ABSTRACT

This invention is in the area of molecular biology/virology and presents oligonucleotides with nucleotide-sequences specific for SI HIV-1 strains. These oligonucleotides may be used for in vitro determination of biological phenotype of HIV-1 strain in biological material from HIV-infected individuals by a number of techniques such as Southern and Northern blot analysis, PCR, NASBA, in situ hybridization, branched DNA hybridization, heteroduplex tracing hybridization and liquid hybridizations. HIV-1 phenotyping may i.e. be used as a diagnostic marker for disease progression or for testing efficacy of antiviral therapy.

8 Claims, 9 Drawing Sheets

OTHER PUBLICATIONS

Figure 1:
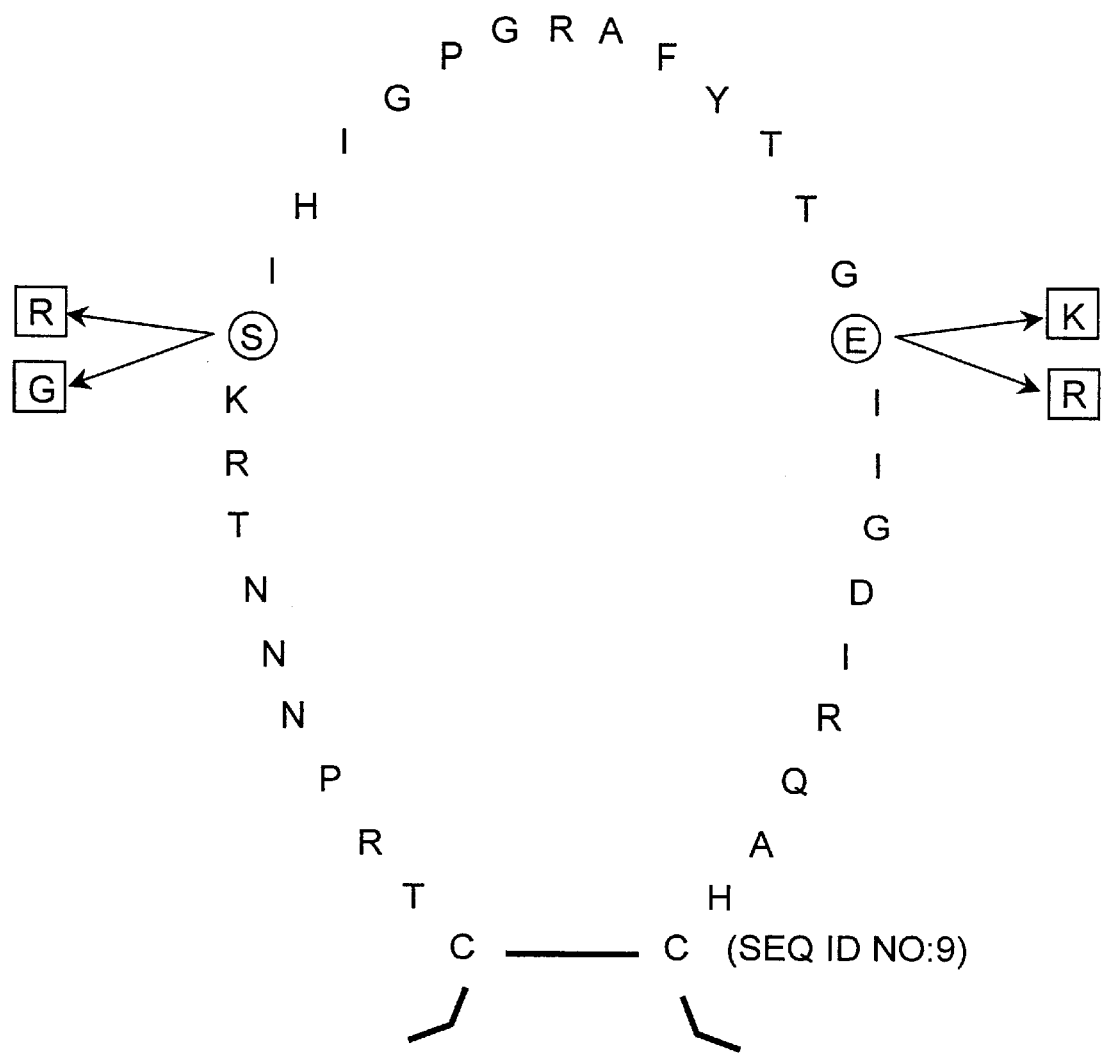

Boswell et al., 1988, "Sequence Comparison and Alignment: The Measurement and Interpretation of Sequence Similarity," in *Computational Molecular Biology: Sources and Methods for Sequence Analysis*, Lesk, A., ed., Oxford University Press, New York, pp. 161–178.*

Wallace et al., 1987, "Oligonucleotide Probes for the Screening of Recombinant DNA Libraries," Methods Enzymol. 152:432–443.*

Sambrook et al., 1989, "Molecular Cloning: A Laboratory Manual", Cold Spring Harbor Laboratory Press, p. 11.47.*

Myers et al., ed., 1993, Human Retroviruses and AIDS: A Compiliation and Analysis of Nucleic Acid and Amino Acid Sequences, Los Alamos National Laboratory, Los Alamos, New Mexico, pp. 123–148.*

Fouchier R. et al., Phenotype–associated sequence variation in the third variable domain of the human immunodeficiency virus type 1 gp 120 molecule, J. Virol. 66(5):3183–3187, May 1992.*

M.P.E.P., paragraph No. 2173.05(h), 1996.*

* cited by examiner-

```
                          306            320
                           |              |
CONSENSUS     CTRPNNNTRKSI.HI..GPGRAFYTTGEIIGDIRQAHC (SEQ ID NO:9)
H72-1.N       -------------.--..----------------------- (SEQ ID NO:105)
M102.N        -------------.--..----------------------- (SEQ ID NO:9)
SCE2.N        -------------.--..----------------------- (SEQ ID NO:9)
SCW44.N       -------------.--..----------------------- (SEQ ID NO:9)
H1140G8.N     ----H--------.--..----------------------- (SEQ ID NO:37)
H1186.N       -------------.--..--------D-------------- (SEQ ID NO:49)
H138G10.N     ----------G-.--..------------------------ (SEQ ID NO:11)
H139A8.N      -------------.--..------A---------------- (SEQ ID NO:64)
H139H9.N      -------------.P-..----------------------- (SEQ ID NO:69)
H157.N        -------------.N-..----------------------- (SEQ ID NO:71)
H169-13.N     ----------G-.--..------------------------ (SEQ ID NO:11)
H172PBL.N     -------------.--..------A---------------- (SEQ ID NO:65)
H373.N        -------------.--..------------------N----- (SEQ ID NO:92)
H455B4.N      ----H--------.--..----------------------- (SEQ ID NO:37)
H455.N        -------------.N-..----------------------- (SEQ ID NO:71)
H500B2.N      -------------.P-..----------------------- (SEQ ID NO:69)
H500.N        -------------.N-..----------------------- (SEQ ID NO:71)
H505.N        -------------.--..------------------N----- (SEQ ID NO:92)
H571-H10.N    -------------.T-..----------------------- (SEQ ID NO:124)
H638.N        ----------G-.--..------------------------ (SEQ ID NO:11)
IIIBAL.N      -------------.--..------L---------------- (SEQ ID NO:151)
M102.N        -------------.--..---------------------Y- (SEQ ID NO:169)
M102.N        -------------.--..----------------V------ (SEQ ID NO:170)
M13750.N      ----------G-.--..------------------------ (SEQ ID NO:11)
M137.N        -------------.-M..----------------------- (SEQ ID NO:185)
S101.N        -------------.--..------V---------------- (SEQ ID NO:186)
S105.N        -------------.--..--------Q-------------- (SEQ ID NO:188)
S163.N        ----------G-.--..------------------------ (SEQ ID NO:11)
S182.N        -------------.N-..----------------------- (SEQ ID NO:71)
SCE5.N        -------------.--..-S--------------------- (SEQ ID NO:254)
SCE7.N        ------I-----.--..------------------------ (SEQ ID NO:255)
SCE8.N        ------I-----.--..------------------------ (SEQ ID NO:256)
H1171.N       -I-----------.N-..----------------------- (SEQ ID NO:38)
H1186A6.N     -------------.P-..--------D-------------- (SEQ ID NO:39)
H1186C2.N     -------------.--..---S----D-------------- (SEQ ID NO:44)
H1186C5.N     -------------.--..---K----D-------------- (SEQ ID NO:45)
H1186E3.N     -------------.N-..--------G-------------- (SEQ ID NO:47)
H1186H4.N     -------------.--..----L---D-------------- (SEQ ID NO:48)
H1234A9.N     -------------.--..---L----D-------------- (SEQ ID NO:51)
H138C10.N     ----------G-.--..--------D-------------- (SEQ ID NO:55)
H138D5.N      ----------D-.--..--------D-------------- (SEQ ID NO:56)
H138F12.N     ----------G-.--..------A---------------- (SEQ ID NO:59)
H139A6.N      -I-----------.N-..----------------------- (SEQ ID NO:38)
H139F4.N      -------------.Y-..------A---------------- (SEQ ID NO:67)
H157.N        -------------.T-..------------------N----- (SEQ ID NO:72)
H1682.N       -------------.--..------A--D------------- (SEQ ID NO:75)
H169-16.N     ----------G-.--..--------D-------------- (SEQ ID NO:55)
H172BAL.N     -------------.--..------AP--------------- (SEQ ID NO:78)
H39-14.N      -------------.S-..------------------N----- (SEQ ID NO:93)
H39-2.N       -------------.S-..----------------I----- (SEQ ID NO:95)
H437.N        ----------G-.--..--------D-------------- (SEQ ID NO:55)
H455A2.N      ----H--------.N-..----------------------- (SEQ ID NO:104)
H500B3.N      -------------.P-..------A---------------- (SEQ ID NO:118)
H500E4.N      -------------.P-..--------D-------------- (SEQ ID NO:119)
H500.N        -I-----------.P-..----------------------- (SEQ ID NO:120)
```

*FIG. 2A*

```
                          306              320
                           |                |
CONSENSUS     CTRPNNNTRKSI.HI..GPGRAFYTTGEIIGDIRQAHC (SEQ ID NO:9)
H571.N        ------------.T-..--------D----------- (SEQ ID NO:125)
H617-18.N     ------------.N-..------A------------- (SEQ ID NO:132)
H617-4.N      ------------.N-..------F------------- (SEQ ID NO:133)
H702.N        ------------.--..A------A------------ (SEQ ID NO:135)
H704-6.N      ------------.N-..------W------------- (SEQ ID NO:137)
H704-8.N      ------------.---..-----W----N-------- (SEQ ID NO:139)
H8321.N       ------------.---..---------G-----Q---- (SEQ ID NO:150)
K114.N        ------------.---..-----W----D--------- (SEQ ID NO:156)
K13396.N      ------------.---..---K------D--------- (SEQ ID NO:166)
M10218.N      ------------.---..--------------V------Y- (SEQ ID NO:167)
M10229.N      ------------.---..----------D-V------- (SEQ ID NO:168)
M13746.N      ------------.QM..-------------------- (SEQ ID NO:178)
M13751.N      ------------.NM..-------------------- (SEQ ID NO:181)
M13757.N      ------------.-M..---K---------------- (SEQ ID NO:182)
S105BAL2.N    ------------.---..-------S--Q--------- (SEQ ID NO:187)
S150SP.S      ------------.-M..---------K---------- (SEQ ID NO:195)
S1693.N       ----------G-.---..------A------------ (SEQ ID NO:59)
S176BM.N      ------------.N-..-------A------------ (SEQ ID NO:211)
S178.N        ----S-------.---..--------D---------- (SEQ ID NO:212)
S179.N        ----------G-.---..-----T------------- (SEQ ID NO:213)
S180.N        ------------.---..----S-V------------ (SEQ ID NO:214)
SCE1.N        ------------.---..------A--D---------- (SEQ ID NO:75)
H1186A1.N     ------------.---..-L---L----D--------- (SEQ ID NO:40)
H1186A5.N     ------------.---..---ST-----D--------- (SEQ ID NO:42)
H1186B2.N     ----------Q-.-P-..----------D--------- (SEQ ID NO:43)
H1186D4.N     ------------.-P-..-L--------D--------- (SEQ ID NO:46)
H138C1.N      ----------G-.---..----------D-R------- (SEQ ID NO:54)
H138F8.N      ----------G-.---..------A--D---------- (SEQ ID NO:60)
H139H12.N     ------------.Y-..-------A-------I---- (SEQ ID NO:68)
H157-17.N     ----------R--.T-..-------------N------ (SEQ ID NO:70)
H168.S        ----------R--.---..---------Q---N------ (SEQ ID NO:76)
H23911.N      ----S-------.---..------A--D---------- (SEQ ID NO:86)
H39.N         ------------.S-..-------A--D---------- (SEQ ID NO:100)
H53.N         ------------.P-..-------A--D---------- (SEQ ID NO:121)
H569.N        ------------.---..A------A--D---------- (SEQ ID NO:122)
H6311.N       ------------.N-..-------A--A---------- (SEQ ID NO:134)
H704-4.N      ------------.---..------W-----V--N---- (SEQ ID NO:136)
K114112.N     ------------.S-..-----W----D--------- (SEQ ID NO:153)
K114.N        ------------.---..-----W----D---N------ (SEQ ID NO:157)
K114.N        ------------.P-..-----W----D--------- (SEQ ID NO:158)
K12769.N      ------------.S-..-----W----D--------- (SEQ ID NO:153)
K13388.N      ------------.---..---K---A--D--------- (SEQ ID NO:163)
K13394.N      ------------.---..---K------D------Y-- (SEQ ID NO:165)
M110.N        ----S-----G-.---..----------T--------- (SEQ ID NO:171)
M114.N        ------------.P-..-----W----D--------- (SEQ ID NO:158)
M13381.N      --------RG-.---..----------D--------- (SEQ ID NO:177)
M13747.N      ----------G-.-M..---K---------------- (SEQ ID NO:179)
M13749.N      ------------.QM..---K---------------- (SEQ ID NO:180)
S151PBL.N     ------------.P-..-----I----D--------- (SEQ ID NO:196)
S168.N        ------------.N-..-------A--D---------- (SEQ ID NO:207)
S16.S         ----------G-.---..-----V----R--------- (SEQ ID NO:209)
S199F11.N     ----------G-.---..------A--D---------- (SEQ ID NO:60)
S200.N        ----------G-.---..------A--D---------- (SEQ ID NO:60)
S205PBL.N     ------------.P-..-------A--D---------- (SEQ ID NO:121)
S24.N         ------------.PM..----------D--------- (SEQ ID NO:238)
```

*FIG. 2B*

```
                          306              320
                           |                |
CONSENSUS     CTRPNNNTRKSI.HI..GPGRAFYTTGEIIGDIRQAHC  (SEQ ID NO:9)
S44.N         ------------.-L..---K------D---------  (SEQ ID NO:243)
SCE10.N       ----S-------.--..-------A---A--------  (SEQ ID NO:251)
SCE9.N        ----S-------.--..-------A---V--------  (SEQ ID NO:257)
H1186A3.N     ------------.--..-L---L-I--D---------  (SEQ ID NO:41)
H138H5.N      ----------G-.--..---G---A--D---------  (SEQ ID NO:61)
H139E9.N      ----G-------.N-..-------A--A---------  (SEQ ID NO:66)
H1681.N       ----------G-.-M..-------A--D---------  (SEQ ID NO:74)
H169-12.N     ------------.P-..------LA-A----------  (SEQ ID NO:77)
H1826.N       ------------.N-..-------A--A------R--  (SEQ ID NO:79)
H199BAL.N     ----------G-.--..------AA-A----------  (SEQ ID NO:82)
H199PBL.N     ----------G-.--..------AA-A----------  (SEQ ID NO:82)
H3202A21.N    ----------G-.--..---K---A--Q---------  (SEQ ID NO:87)
H354.N        ---------R--.--..----WA--D-----------  (SEQ ID NO:90)
H479.S        --------QG-.--...---------RR---------  (SEQ ID NO:108)
H571-143.N    ---------R--.T-..-------A----T-------  (SEQ ID NO:123)
K11491.N      ------------.SK..------W----D--------  (SEQ ID NO:154)
K11493.N      -----------N.--..------W----D---N----  (SEQ ID NO:155)
K114.N        ------------.P-..------W----D---N----  (SEQ ID NO:159)
K13392.N      ---------RG-.--..-------A--D---------  (SEQ ID NO:164)
M133.N        ---------RG-.N-..---------D----------  (SEQ ID NO:176)
M13768.N      ----------G-.QM..---K----------------  (SEQ ID NO:183)
M13771.N      ------------.QM..---K-----------E----  (SEQ ID NO:184)
S206.N        ---------R--.P-..-------A--Q---------  (SEQ ID NO:225)
S150PBL.S     ----------G-.--..-----I---SK---------  (SEQ ID NO:194)
S183.N        ------------.GL..-------A--D---------  (SEQ ID NO:216)
S199C11.N     ----------G-.--..---S---A--D---------  (SEQ ID NO:219)
S199D9.N      ----------G-.--..----FA--D-----------  (SEQ ID NO:221)
S199.N        ----------G-.--..---K---A--D---------  (SEQ ID NO:217)
SCE4.N        ----S-------.--..-S-----A---V--------  (SEQ ID NO:253)
H1186.N       ------------.QL..---K-L----D---------  (SEQ ID NO:50)
H138H6.N      ----------G-.--..---G---A--D-----I---  (SEQ ID NO:62)
H159.N        ------------.NM..-----I----Q-V-------  (SEQ ID NO:73)
H186.N        -I--G-------.P-..-------A--D---------  (SEQ ID NO:81)
H224.N        ----------G-.-L..-----WF-----------K-  (SEQ ID NO:83)
H3202A3.N     ----------G-.-M..---K---A--Q---------  (SEQ ID NO:88)
H320.S        ----------G-.--..------AARK----------  (SEQ ID NO:89)
H449.N        ------------.SM..---K------A---N-----  (SEQ ID NO:103)
H4791.N       ----------G-.N-..-------A--Q---N-----  (SEQ ID NO:106)
H4798.S       --------QG-.Y-...---------RR---------  (SEQ ID NO:107)
H6002A11.N    -V----------.S-..-------A--D---N-----  (SEQ ID NO:127)
H6002H9.N     -V----------.P-..-------A--D---N-----  (SEQ ID NO:129)
H6002.N       -V----------.Y-..-------A--D---N-----  (SEQ ID NO:126)
H6042C6.N     -V----------.P-..-------A--D---N-----  (SEQ ID NO:129)
H617-17.N     ---------R--.N-..----FA--D-----------  (SEQ ID NO:131)
H7041.S       ---------RV.TM...----L---------------  (SEQ ID NO:140)
M11477.N      -S-------V--.P-..------W----D--------  (SEQ ID NO:173)
S206.N        ---------KR-.S-..-------A--K---------  (SEQ ID NO:226)
S119MDM.N     ---------R--.--..-A-----A--A------K--  (SEQ ID NO:190)
S119.N        ------------.--..-A-S---A--A------K--  (SEQ ID NO:189)
S201PBL.S     ----------G-.--..------AA-RV---------  (SEQ ID NO:224)
S32.S         ----S-------.R-HR..----------N--------  (SEQ ID NO:239)
S96MDM.N      ----H----RG-.--..---------S-T--------  (SEQ ID NO:247)
SCE3.N        -I--S-------.--..-------A--DV--------  (SEQ ID NO:252)
H138E2.S      ------------.E-..---L--R---RK--------  (SEQ ID NO:57)
H224-40.N     ----------G-.-L..-----WFA----------K-  (SEQ ID NO:84)
```

*FIG. 2C*

```
                306             320
                 |               |
CONSENSUS    CTRPNNNTRKSI.HI..GPGRAFYTTGEIIGDIRQAHC  (SEQ ID NO:9)
H373385.S    -------I-RRMI--..----------------N------  (SEQ ID NO:91)
H39-19.S     ----------R-.SL..S---V-------R--------  (SEQ ID NO:94)
H39.S        ----------R-.SL..S---V-----------R---  (SEQ ID NO:101)
H491A9.N     ----G----R--.P-..---K--F--.----------  (SEQ ID NO:117)
H6002D9.N    -V----------.Y-..--------AI-D---N------  (SEQ ID NO:128)
H6042.N      -V----------.Y-..--------A--D---KR-----  (SEQ ID NO:130)
M114.N       -S-------R-V.--..------W----D---N------  (SEQ ID NO:172)
S212-120.N   ------------.--..---Q---ANSR------N---  (SEQ ID NO:235)
S206.N       -------IKR--.S-..--------A--K---------  (SEQ ID NO:227)
S206.N       --------R--.P-..---G---A-ER---------  (SEQ ID NO:228)
S206.N       -------IKR--.S-..--------A--Q---------  (SEQ ID NO:229)
S148PBL.N    ---------G-.-L..---GT--A--D----------  (SEQ ID NO:193)
S164-40.N    ------------.--..--------G-.D-V-N----Y-  (SEQ ID NO:201)
S175.S       ---------RG-.Y-..-----V--K-R---------  (SEQ ID NO:210)
S200G8.S     ---------G-.R-..-----V-A-EK---------  (SEQ ID NO:223)
S961.N       ---------R--.--..------FG-.D---N------  (SEQ ID NO:245)
S962.N       ---------RG-.--..-------G-.D---N------  (SEQ ID NO:246)
H138.S       ---------RD-.--..-L--R----.RK---------  (SEQ ID NO:63)
H39-60.S     ------V--R-.SL..S---V-----------K---  (SEQ ID NO:96)
H39-9.S      ---F------R-.SL..S---V-------R--------  (SEQ ID NO:99)
H39.S        -------I--R-.SL..S---V-----------K---  (SEQ ID NO:102)
H486C10.S    ----G---KR--.Y-..-------H--DR---------  (SEQ ID NO:111)
H486E11.N    ----G----R--.P-..---K--F--.Q---------  (SEQ ID NO:113)
H486F11.N    ----G---KR--.P-..---K--F--.----------  (SEQ ID NO:114)
H486F2.N     ----G----R--.P-..---KV-F--.----------  (SEQ ID NO:115)
H704.S       ----------RV.TM..----VW--------N------  (SEQ ID NO:141)
H72-25.S     ---------RR-.R-..-------R-I-Q---N------  (SEQ ID NO:144)
H72.S        ------Y--RR-.S-..-------R-M-Q---------  (SEQ ID NO:148)
H72.S        ---------RR-.S-..-------R-I-Q---N------  (SEQ ID NO:149)
K127.N       -I----------.TF..---Q---A-SN---------  (SEQ ID NO:160)
S212.N       ------------.--..---Q---ANSP---N----Y-  (SEQ ID NO:234)
S213-101.N   -I------Q--.--..---Q---ANSP---------  (SEQ ID NO:236)
S213-102.N   -I------Q--.--..---Q---AHSP---------  (SEQ ID NO:237)
S206.N       -------IKR--.SM..--------A--Q---------  (SEQ ID NO:230)
S206.N       -------IKR--.S-..--------A--Q------V--  (SEQ ID NO:231)
S127.S       ----------RV.TM..----VL----------K---  (SEQ ID NO:192)
S165-28.N    ---LS---RGV.--..----------TV---------  (SEQ ID NO:203)
S165.N       ---LS---RGV.--..----------AV---------  (SEQ ID NO:205)
S181.N       ------------.PM..---K---A--D------K-Y-  (SEQ ID NO:215)
SCA-B.N      ------------V.R-..---QT--A--D---N------  (SEQ ID NO:250)
H138A2.S     ---------RD-.--..-L--R----.RK-----I----  (SEQ ID NO:52)
H224-42.S    ------Y---G-.-L..------WL--RK------K---  (SEQ ID NO:85)
H486A3.S     ----G---KR--.Y-..-------H--DR-----R---  (SEQ ID NO:110)
H486C5.S     ----G---KR--.Y-..-------Q--DR-----R---  (SEQ ID NO:112)
H486H3.S     ----G---KR--.Y-..-------H--DR-----K---  (SEQ ID NO:116)
H486.N       ----G---KR--.P-..---KV-F--.----------  (SEQ ID NO:109)
H704-7.S     ----------RV.TM..----VW----V---N------  (SEQ ID NO:138)
H704.S       ----------RV.TM..----VW--------N-K----  (SEQ ID NO:142)
H72-28.S     --------I-RR-.S..-------R-I-Q---N------  (SEQ ID NO:145)
H72-2.S      --------K-RR-.I..-------R-I-Q---N------  (SEQ ID NO:146)
K127.N       -I----------.TF..---Q---A-SN--------Y-  (SEQ ID NO:162)
S206.N       -------IKR--.SM..--------A--Q------E---  (SEQ ID NO:232)
S127-17.S    ----------RV.TM..----VW--------N-K----  (SEQ ID NO:191)
S164.N       --------K-Q--.--..------FG-.D---N----Y-  (SEQ ID NO:197)
S165-37.N    ---LS---RGV.--..----------AV------G--  (SEQ ID NO:204)
```

*FIG. 2D*

```
                    306              320
                     |                |
CONSENSUS   CTRPNNNTRKSI.HI..GPGRAFYTTGEIIGDIRQAHC  (SEQ ID NO:9)
S1691.S     ----------G-RIGHI----V-----K----------  (SEQ ID NO:208)
S1692.S     ----------G-RIGHI----V-----K----------  (SEQ ID NO:208)
S199A9.S    ------Y---G-.R-..-----V-AAEK----------  (SEQ ID NO:218)
S199D7.S    ----------G-.R-..---S-VIA-EK----------  (SEQ ID NO:220)
S200F3.S    ------Y---G-.R-..-----VIA-EK----------  (SEQ ID NO:222)
S200G9.S    ------Y---G-.R-..-----V-AAEK----------  (SEQ ID NO:258)
S37.S       ----------RV.TL..----VW-----------K-Y-  (SEQ ID NO:240)
SCA-4A11.N  ----G------V.R-..---QT--A--A---N------  (SEQ ID NO:248)
H138B3.S    ----------RD-.--..---L--R---.RK-K--V-----  (SEQ ID NO:53)
H72-15.S    ------Y--RRL.S-..-------R-I-Q---N------  (SEQ ID NO:143)
H72-8.S     ---------RRV.S-..-------R-I-Q---NT-----  (SEQ ID NO:147)
K12761.N    -I--------.TF..----Q---A-SN---N----Y-   (SEQ ID NO:161)
M127.N      -I--------.TF..----Q---A-SN-----K--Y-   (SEQ ID NO:175)
M127.N      -I--------.TF..----Q---A-SN---N----Y-   (SEQ ID NO:161)
S206.N      -------KKR--.P-..----G---A-ER------E---  (SEQ ID NO:233)
S42.S       -------IKRR-I--..--------HA--G-.-------- (SEQ ID NO:242)
SCA-4F9.N   ----G------V.R-..---QT--A--A-T-N------   (SEQ ID NO:249)
H39-65.S    --------I--R-.SL..S---VY------R----K-Y-  (SEQ ID NO:97)
H39-67.S    --------V--R-.SL..S---VY------R----K-Y-  (SEQ ID NO:98)
M12737.N    -I------K---.TF..----Q---A-SN---N----Y-  (SEQ ID NO:174)
H18269.S    ---LSA-KIRHM.---..---------A--K------K--- (SEQ ID NO:80)
IIIB.S      ----------R-.R-QR------V-.IGK--NM-----   (SEQ ID NO:152)
S55.S       --------K-G-.AV..----DI--ADK----LK----   (SEQ ID NO:244)
S164-18.S   -----R-KIRR-.---..----P--G-.D-E-P----Y-  (SEQ ID NO:198)
S164-26.S   -----R-RIRR-.---..----P--G-.D-E-T----Y-  (SEQ ID NO:200)
S164-28.S   -----R-KIRR-.---..----P--G-.D-E-P----Y-  (SEQ ID NO:198)
S164-23.S   ----TR-KIRR-.---..----P--G-.D-T-P----Y-  (SEQ ID NO:199)
S165.S      ---LS-----RGVHIKHI----V-----AV-----R---  (SEQ ID NO:206)
S165-27.S   ---LG-K--RGVHIKHI----V-----AV-----R---   (SEQ ID NO:202)
```

*FIG. 2E*

```
                           SEQUENCE LISTING (1) GENERAL INFORMATION:

(iii) NUMBER OF SEQUENCES: 257

(2) INFORMATION FOR SEQ ID NO: 1:

(i) SEQUENCE CHARACTERISTICS:
         (A) LENGTH: 11 base pairs
         (B) TYPE: nucleic acid
         (C) STRANDEDNESS: unknown
         (D) TOPOLOGY: unknown (ii) MOLECULE TYPE: other nucleic acid (iii) HYPOTHETICAL: NO (xi) SEQUENCE DESCRIPTION: SEQ ID NO: 1:

CCTATTATTT T                                                              11

(2) INFORMATION FOR SEQ ID NO: 2:

(i) SEQUENCE CHARACTERISTICS:
         (A) LENGTH: 11 base pairs
         (B) TYPE: nucleic acid
         (C) STRANDEDNESS: unknown
         (D) TOPOLOGY: unknown (ii) MOLECULE TYPE: other nucleic acid (iii) HYPOTHETICAL: NO (xi) SEQUENCE DESCRIPTION: SEQ ID NO: 2:

CCTATTATTC T                                                              11

(2) INFORMATION FOR SEQ ID NO: 3:

(i) SEQUENCE CHARACTERISTICS:
         (A) LENGTH: 11 base pairs
         (B) TYPE: nucleic acid
         (C) STRANDEDNESS: unknown
```

(D) TOPOLOGY: unknown (ii) MOLECULE TYPE: other nucleic acid (iii) HYPOTHETICAL: NO (xi) SEQUENCE DESCRIPTION: SEQ ID NO: 3:

CAAGAAAAAG G                                                              11

(2) INFORMATION FOR SEQ ID NO: 4:

(i) SEQUENCE CHARACTERISTICS:
          (A) LENGTH: 11 base pairs
          (B) TYPE: nucleic acid
          (C) STRANDEDNESS: unknown
          (D) TOPOLOGY: unknown (ii) MOLECULE TYPE: other nucleic acid (iii) HYPOTHETICAL: NO (xi) SEQUENCE DESCRIPTION: SEQ ID NO: 4:

CAAGAAAAAG A                                                              11

(2) INFORMATION FOR SEQ ID NO: 5:

(i) SEQUENCE CHARACTERISTICS:
          (A) LENGTH: 20 base pairs
          (B) TYPE: nucleic acid
          (C) STRANDEDNESS: unknown
          (D) TOPOLOGY: unknown (ii) MOLECULE TYPE: other nucleic acid (iii) HYPOTHETICAL: NO (xi) SEQUENCE DESCRIPTION: SEQ ID NO: 5:

CTTATATCTC CTATTATTTT                                                     20

(2) INFORMATION FOR SEQ ID NO: 6:

(i) SEQUENCE CHARACTERISTICS:
          (A) LENGTH: 20 base pairs
          (B) TYPE: nucleic acid
          (C) STRANDEDNESS: unknown
          (D) TOPOLOGY: unknown (ii) MOLECULE TYPE: other nucleic acid (iii) HYPOTHETICAL: NO (xi) SEQUENCE DESCRIPTION: SEQ ID NO: 6:

CTTATATCTC CTATTATTCT                                                     20

(2) INFORMATION FOR SEQ ID NO: 7:

(i) SEQUENCE CHARACTERISTICS:
          (A) LENGTH: 20 base pairs
          (B) TYPE: nucleic acid
          (C) STRANDEDNESS: unknown
          (D) TOPOLOGY: unknown (ii) MOLECULE TYPE: other nucleic acid (iii) HYPOTHETICAL: NO (xi) SEQUENCE DESCRIPTION: SEQ ID NO: 7:

ACAACAATAC AAGAAAAAGG                                                     20

(2) INFORMATION FOR SEQ ID NO: 8:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: other nucleic acid (iii) HYPOTHETICAL: NO (xi) SEQUENCE DESCRIPTION: SEQ ID NO: 8:

ACAACAATAC AAGAAAAAGA                                      20

(2) INFORMATION FOR SEQ ID NO: 9:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 9:

Cys Thr Arg Pro Asn Asn Asn Thr Arg Lys Ser Ile His Ile Gly Pro
1          5                   10              15

Gly Arg Ala Phe Tyr Thr Thr Gly Glu Ile Ile Gly Asp Ile Arg Gln
          20                 25                30

Ala His Cys
      35

(2) INFORMATION FOR SEQ ID NO: 10:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 10:

Cys Thr Arg Pro Asn Asn Asn Thr Arg Lys Arg Ile His Ile Gly Pro
1          5                   10              15

Gly Arg Ala Phe Tyr Thr Thr Gly Glu Ile Ile Gly Asp Ile Arg Gln
          20                 25                30

Ala His Cys
      35

(2) INFORMATION FOR SEQ ID NO: 11:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 11:

```
Cys Thr Arg Pro Asn Asn Asn Thr Arg Lys Gly Ile His Ile Gly Pro
1               5                   10                  15

Gly Arg Ala Phe Tyr Thr Thr Gly Glu Ile Ile Gly Asp Ile Arg Gln
            20                  25                  30

Ala His Cys
        35
```

(2) INFORMATION FOR SEQ ID NO: 12:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 12:

```
Cys Thr Arg Pro Asn Asn Asn Thr Arg Lys Ser Ile His Ile Gly Pro
1               5                   10                  15

Gly Arg Ala Phe Tyr Thr Thr Gly Lys Ile Ile Gly Asp Ile Arg Gln
            20                  25                  30

Ala His Cys
        35
```

(2) INFORMATION FOR SEQ ID NO: 13:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 13:

```
Cys Thr Arg Pro Asn Asn Asn Thr Arg Lys Ser Ile His Ile Gly Pro
1               5                   10                  15

Gly Arg Ala Phe Tyr Thr Thr Gly Arg Ile Ile Gly Asp Ile Arg Gln
            20                  25                  30

Ala His Cys
        35
```

(2) INFORMATION FOR SEQ ID NO: 14:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 14:

```
Cys Thr Arg Pro Asn Asn Asn Thr Arg Lys Arg Ile His Ile Gly Pro
1               5                   10                  15

Gly Arg Ala Phe Tyr Thr Thr Gly Lys Ile Ile Gly Asp Ile Arg Gln
            20                  25                  30

Ala His Cys
```

35

(2) INFORMATION FOR SEQ ID NO: 15:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 15:

Cys Thr Arg Pro Asn Asn Asn Thr Arg Lys Arg Ile His Ile Gly Pro
1               5                   10                  15

Gly Arg Ala Phe Tyr Thr Thr Gly Arg Ile Ile Gly Asp Ile Arg Gln
            20                  25                  30

Ala His Cys
        35

(2) INFORMATION FOR SEQ ID NO: 16:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 16:

Cys Thr Arg Pro Asn Asn Asn Thr Arg Lys Gly Ile His Ile Gly Pro
1               5                   10                  15

Gly Arg Ala Phe Tyr Thr Thr Gly Lys Ile Ile Gly Asp Ile Arg Gln
            20                  25                  30

Ala His Cys
        35

(2) INFORMATION FOR SEQ ID NO: 17:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 17:

Cys Thr Arg Pro Asn Asn Asn Thr Arg Lys Gly Ile His Ile Gly Pro
1               5                   10                  15

Gly Arg Ala Phe Tyr Thr Thr Gly Arg Ile Ile Gly Asp Ile Arg Gln
            20                  25                  30

Ala His Cys
        35

(2) INFORMATION FOR SEQ ID NO: 18:

(i) SEQUENCE CHARACTERISTICS:
        (A) LENGTH: 20 base pairs (B) TYPE: nucleic acid
        (C) STRANDEDNESS: unknown
        (D) TOPOLOGY: linear (ii) MOLECULE TYPE: other nucleic acid (iii) HYPOTHETICAL: NO (xi) SEQUENCE DESCRIPTION: SEQ ID NO: 18:

TACAATGTAC ACATGGAATT                                                    20

(2) INFORMATION FOR SEQ ID NO: 19:

(i) SEQUENCE CHARACTERISTICS:
        (A) LENGTH: 20 base pairs
        (B) TYPE: nucleic acid
        (C) STRANDEDNESS: unknown
        (D) TOPOLOGY: linear (ii) MOLECULE TYPE: other nucleic acid (iii) HYPOTHETICAL: NO (xi) SEQUENCE DESCRIPTION: SEQ ID NO: 19:

TGGCAGTCTA GCAGAAGAAG                                                    20

(2) INFORMATION FOR SEQ ID NO: 20:

(i) SEQUENCE CHARACTERISTICS:
        (A) LENGTH: 20 base pairs
        (B) TYPE: nucleic acid
        (C) STRANDEDNESS: unknown
        (D) TOPOLOGY: linear (ii) MOLECULE TYPE: other nucleic acid (iii) HYPOTHETICAL: NO (xi) SEQUENCE DESCRIPTION: SEQ ID NO: 20:

TCTGGGTCCC CTCCTGAGGA                                                    20

(2) INFORMATION FOR SEQ ID NO: 21:

(i) SEQUENCE CHARACTERISTICS:
        (A) LENGTH: 20 base pairs
        (B) TYPE: nucleic acid
        (C) STRANDEDNESS: unknown
        (D) TOPOLOGY: linear (ii) MOLECULE TYPE: other nucleic acid (iii) HYPOTHETICAL: NO (xi) SEQUENCE DESCRIPTION: SEQ ID NO: 21:

ATTACAGTAG AAAAATTCCC                                                    20

(2) INFORMATION FOR SEQ ID NO: 22:

(i) SEQUENCE CHARACTERISTICS:
        (A) LENGTH: 20 base pairs
        (B) TYPE: nucleic acid
        (C) STRANDEDNESS: unknown
        (D) TOPOLOGY: linear (ii) MOLECULE TYPE: other nucleic acid (iii) HYPOTHETICAL: NO (xi) SEQUENCE DESCRIPTION: SEQ ID NO: 22:

ACAACAATAC AAGAAAAAGT                                                    20

(2) INFORMATION FOR SEQ ID NO: 23:

(i) SEQUENCE CHARACTERISTICS:
        (A) LENGTH: 20 base pairs
        (B) TYPE: nucleic acid
        (C) STRANDEDNESS: unknown
        (D) TOPOLOGY: linear (ii) MOLECULE TYPE: other nucleic acid (iii) HYPOTHETICAL: NO (xi) SEQUENCE DESCRIPTION: SEQ ID NO: 23:

ACAACAATAC AAGAAAAGGT                                        20

(2) INFORMATION FOR SEQ ID NO: 24:

(i) SEQUENCE CHARACTERISTICS:
        (A) LENGTH: 20 base pairs
        (B) TYPE: nucleic acid
        (C) STRANDEDNESS: unknown
        (D) TOPOLOGY: linear (ii) MOLECULE TYPE: other nucleic acid (iii) HYPOTHETICAL: NO (xi) SEQUENCE DESCRIPTION: SEQ ID NO: 24:

ACAACAATAC AAGACAAGGT                                        20

(2) INFORMATION FOR SEQ ID NO: 25:

(i) SEQUENCE CHARACTERISTICS:
        (A) LENGTH: 20 base pairs
        (B) TYPE: nucleic acid
        (C) STRANDEDNESS: unknown
        (D) TOPOLOGY: linear (ii) MOLECULE TYPE: other nucleic acid (iii) HYPOTHETICAL: NO (xi) SEQUENCE DESCRIPTION: SEQ ID NO: 25:

ACAACAATAC AAGAAAAAGG                                        20

(2) INFORMATION FOR SEQ ID NO: 26:

(i) SEQUENCE CHARACTERISTICS:
        (A) LENGTH: 20 base pairs
        (B) TYPE: nucleic acid
        (C) STRANDEDNESS: unknown
        (D) TOPOLOGY: linear (ii) MOLECULE TYPE: other nucleic acid (iii) HYPOTHETICAL: NO (xi) SEQUENCE DESCRIPTION: SEQ ID NO: 26:

ACAACAATAC AAGAAAAAGA                                        20

(2) INFORMATION FOR SEQ ID NO: 27:

(i) SEQUENCE CHARACTERISTICS:
        (A) LENGTH: 20 base pairs
        (B) TYPE: nucleic acid
        (C) STRANDEDNESS: unknown
        (D) TOPOLOGY: linear (ii) MOLECULE TYPE: other nucleic acid (iii) HYPOTHETICAL: NO (xi) SEQUENCE DESCRIPTION: SEQ ID NO: 27:

GAAATAATAG GAGATATAAG                                                    20

(2) INFORMATION FOR SEQ ID NO: 28:

(i) SEQUENCE CHARACTERISTICS:
            (A) LENGTH: 20 base pairs
            (B) TYPE: nucleic acid
            (C) STRANDEDNESS: unknown
            (D) TOPOLOGY: linear (ii) MOLECULE TYPE: other nucleic acid (iii) HYPOTHETICAL: NO (xi) SEQUENCE DESCRIPTION: SEQ ID NO: 28:

AAAATAATAG GAGATATAAG                                                    20

(2) INFORMATION FOR SEQ ID NO: 29:

(i) SEQUENCE CHARACTERISTICS:
            (A) LENGTH: 20 base pairs
            (B) TYPE: nucleic acid
            (C) STRANDEDNESS: unknown
            (D) TOPOLOGY: linear (ii) MOLECULE TYPE: other nucleic acid (iii) HYPOTHETICAL: NO (xi) SEQUENCE DESCRIPTION: SEQ ID NO: 29:

AGAATAATAG GAGATATAAG                                                    20

(2) INFORMATION FOR SEQ ID NO: 30:

(i) SEQUENCE CHARACTERISTICS:
            (A) LENGTH: 20 base pairs
            (B) TYPE: nucleic acid
            (C) STRANDEDNESS: unknown
            (D) TOPOLOGY: linear (ii) MOLECULE TYPE: other nucleic acid (iii) HYPOTHETICAL: NO (xi) SEQUENCE DESCRIPTION: SEQ ID NO: 30:

CAAATAATAG GAAATATAAG                                                    20

(2) INFORMATION FOR SEQ ID NO: 31:

(i) SEQUENCE CHARACTERISTICS:
            (A) LENGTH: 20 base pairs
            (B) TYPE: nucleic acid
            (C) STRANDEDNESS: unknown
            (D) TOPOLOGY: linear (ii) MOLECULE TYPE: other nucleic acid (iii) HYPOTHETICAL: NO (xi) SEQUENCE DESCRIPTION: SEQ ID NO: 31:

GGAAAAATAG GAAATATGAG                                                    20

(2) INFORMATION FOR SEQ ID NO: 32:

(i) SEQUENCE CHARACTERISTICS:

```
       (A) LENGTH: 20 base pairs
       (B) TYPE: nucleic acid
       (C) STRANDEDNESS: unknown
       (D) TOPOLOGY: linear (ii) MOLECULE TYPE: other nucleic acid (iii) HYPOTHETICAL: NO (xi) SEQUENCE DESCRIPTION: SEQ ID NO: 32:

ATAACAATAT AAGAAGAAGG                                              20

(2) INFORMATION FOR SEQ ID NO: 33:

(i) SEQUENCE CHARACTERISTICS:
       (A) LENGTH: 20 base pairs
       (B) TYPE: nucleic acid
       (C) STRANDEDNESS: unknown
       (D) TOPOLOGY: linear (ii) MOLECULE TYPE: other nucleic acid (iii) HYPOTHETICAL: NO (xi) SEQUENCE DESCRIPTION: SEQ ID NO: 33:

ACAACAATAT AAAAAGAAGA                                              20

(2) INFORMATION FOR SEQ ID NO: 34:

(i) SEQUENCE CHARACTERISTICS:
       (A) LENGTH: 20 base pairs
       (B) TYPE: nucleic acid
       (C) STRANDEDNESS: unknown
       (D) TOPOLOGY: linear (ii) MOLECULE TYPE: other nucleic acid (iii) HYPOTHETICAL: NO (xi) SEQUENCE DESCRIPTION: SEQ ID NO: 34:

ACAGAAATAA AATACGAAGG                                              20

(2) INFORMATION FOR SEQ ID NO: 35:

(i) SEQUENCE CHARACTERISTICS:
       (A) LENGTH: 20 base pairs
       (B) TYPE: nucleic acid
       (C) STRANDEDNESS: unknown
       (D) TOPOLOGY: linear (ii) MOLECULE TYPE: other nucleic acid (iii) HYPOTHETICAL: NO (xi) SEQUENCE DESCRIPTION: SEQ ID NO: 35:

AATATAATAG GAGATATAAG                                              20

(2) INFORMATION FOR SEQ ID NO: 36:

(i) SEQUENCE CHARACTERISTICS:
       (A) LENGTH: 20 base pairs
       (B) TYPE: nucleic acid
       (C) STRANDEDNESS: unknown
       (D) TOPOLOGY: linear (ii) MOLECULE TYPE: other nucleic acid (iii) HYPOTHETICAL: NO (xi) SEQUENCE DESCRIPTION: SEQ ID NO: 36:
```

AAAATAATAG GAGATCTAAA                                              20

(2) INFORMATION FOR SEQ ID NO: 37:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 37:

Cys Thr Arg Pro His Asn Asn Thr Arg Lys Ser Ile His Ile Gly Pro
1               5                   10                  15

Gly Arg Ala Phe Tyr Thr Thr Gly Glu Ile Ile Gly Asp Ile Arg Gln
            20                  25                  30

Ala His Cys
        35

(2) INFORMATION FOR SEQ ID NO: 38:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 38:

Cys Ile Arg Pro Asn Asn Asn Thr Arg Lys Ser Ile Asn Ile Gly Pro
1               5                   10                  15

Gly Arg Ala Phe Tyr Thr Thr Gly Glu Ile Ile Gly Asp Ile Arg Gln
            20                  25                  30

Ala His Cys
        35

(2) INFORMATION FOR SEQ ID NO: 39:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 39:

Cys Thr Arg Pro Asn Asn Asn Thr Arg Lys Ser Ile Pro Ile Gly Pro
1               5                   10                  15

Gly Arg Ala Phe Tyr Thr Thr Gly Asp Ile Ile Gly Asp Ile Arg Gln
            20                  25                  30

Ala His Cys
        35

(2) INFORMATION FOR SEQ ID NO: 40:

(i) SEQUENCE CHARACTERISTICS:
        (A) LENGTH: 35 amino acids (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 40:

Cys Thr Arg Pro Asn Asn Asn Thr Arg Lys Ser Ile His Ile Gly Leu
1               5                   10                  15

Gly Arg Ala Leu Tyr Thr Thr Gly Asp Ile Ile Gly Asp Ile Arg Gln
            20                  25                  30

Ala His Cys
        35

(2) INFORMATION FOR SEQ ID NO: 41:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 41:

Cys Thr Arg Pro Asn Asn Asn Thr Arg Lys Ser Ile His Ile Gly Leu
1               5                   10                  15

Gly Arg Ala Leu Tyr Ile Thr Gly Asp Ile Ile Gly Asp Ile Arg Gln
            20                  25                  30

Ala His Cys
        35

(2) INFORMATION FOR SEQ ID NO: 42:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 42:

Cys Thr Arg Pro Asn Asn Asn Thr Arg Lys Ser Ile His Ile Gly Pro
1               5                   10                  15

Gly Ser Thr Phe Tyr Thr Thr Gly Asp Ile Ile Gly Asp Ile Arg Gln
            20                  25                  30

Ala His Cys
        35

(2) INFORMATION FOR SEQ ID NO: 43:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 43:

Cys Thr Arg Pro Asn Asn Asn Thr Arg Gln Ser Ile Pro Ile Gly Pro
1               5                   10                  15

Gly Arg Ala Phe Tyr Thr Thr Gly Asp Ile Ile Gly Asp Ile Arg Gln
            20                  25                  30

Ala His Cys
        35

(2) INFORMATION FOR SEQ ID NO: 44:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 44:

Cys Thr Arg Pro Asn Asn Asn Thr Arg Lys Ser Ile His Ile Gly Pro
1               5                   10                  15

Gly Ser Ala Phe Tyr Thr Thr Gly Asp Ile Ile Gly Asp Ile Arg Gln
            20                  25                  30

Ala His Cys
        35

(2) INFORMATION FOR SEQ ID NO: 45:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 45:

Cys Thr Arg Pro Asn Asn Asn Thr Arg Lys Ser Ile His Ile Gly Pro
1               5                   10                  15

Gly Lys Ala Phe Tyr Thr Thr Gly Asp Ile Ile Gly Asp Ile Arg Gln
            20                  25                  30

Ala His Cys
        35

(2) INFORMATION FOR SEQ ID NO: 46:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 46:

Cys Thr Arg Pro Asn Asn Asn Thr Arg Lys Ser Ile Pro Ile Gly Leu
1               5                   10                  15

Gly Arg Ala Phe Tyr Thr Thr Gly Asp Ile Ile Gly Asp Ile Arg Gln

```
                  20                  25                  30

Ala His Cys
        35

(2) INFORMATION FOR SEQ ID NO: 47:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 47:

Cys Thr Arg Pro Asn Asn Asn Thr Arg Lys Ser Ile Asn Ile Gly Pro
1               5                   10                  15

Gly Arg Ala Phe Tyr Thr Thr Gly Gly Ile Ile Gly Asp Ile Arg Gln
            20                  25                  30

Ala His Cys
        35

(2) INFORMATION FOR SEQ ID NO: 48:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 48:

Cys Thr Arg Pro Asn Asn Asn Thr Arg Lys Ser Ile His Ile Gly Pro
1               5                   10                  15

Gly Arg Ala Leu Tyr Thr Thr Gly Asp Ile Ile Gly Asp Ile Arg Gln
            20                  25                  30

Ala His Cys
        35

(2) INFORMATION FOR SEQ ID NO: 49:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 49:

Cys Thr Arg Pro Asn Asn Asn Thr Arg Lys Ser Ile His Ile Gly Pro
1               5                   10                  15

Gly Arg Ala Phe Tyr Thr Thr Gly Asp Ile Ile Gly Asp Ile Arg Gln
            20                  25                  30

Ala His Cys
        35

(2) INFORMATION FOR SEQ ID NO: 50:
```

```
    (i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 50:

Cys Thr Arg Pro Asn Asn Asn Thr Arg Lys Ser Ile Gln Leu Gly Pro
1               5                  10                  15

Gly Lys Ala Leu Tyr Thr Thr Gly Asp Ile Ile Gly Asp Ile Arg Gln
             20                  25                  30

Ala His Cys
         35

(2) INFORMATION FOR SEQ ID NO: 51:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 51:

Cys Thr Arg Pro Asn Asn Asn Thr Arg Lys Ser Ile His Ile Gly Leu
1               5                  10                  15

Gly Arg Ala Phe Tyr Thr Thr Gly Asp Ile Ile Gly Asp Ile Arg Gln
             20                  25                  30

Ala His Cys
         35

(2) INFORMATION FOR SEQ ID NO: 52:

(i) SEQUENCE CHARACTERISTICS:
        (A) LENGTH: 34 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 52:

Cys Thr Arg Pro Asn Asn Asn Thr Arg Arg Asp Ile His Ile Gly Leu
1               5                  10                  15

Gly Arg Arg Phe Tyr Thr Arg Lys Ile Ile Gly Asp Ile Ile Gln Ala
             20                  25                  30

His Cys (2) INFORMATION FOR SEQ ID NO: 53:

(i) SEQUENCE CHARACTERISTICS:
        (A) LENGTH: 34 amino acids
        (B) TYPE: amino acid
        (C) STRANDEDNESS: unknown
        (D) TOPOLOGY: circular (ii) MOLECULE TYPE: peptide
```

(iii) HYPOTHETICAL: NO (xi) SEQUENCE DESCRIPTION: SEQ ID NO: 53:

Cys Thr Arg Pro Asn Asn Asn Thr Arg Arg Asp Ile His Ile Gly Leu
1               5                   10                  15

Gly Arg Arg Phe Tyr Thr Arg Lys Ile Lys Gly Asp Val Arg Gln Ala
            20                  25                  30

His Cys (2) INFORMATION FOR SEQ ID NO: 54:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 54:

Cys Thr Arg Pro Asn Asn Asn Thr Arg Lys Gly Ile His Ile Gly Pro
1               5                   10                  15

Gly Arg Ala Phe Tyr Thr Thr Gly Asp Ile Arg Gly Asp Ile Arg Gln
            20                  25                  30

Ala His Cys
        35

(2) INFORMATION FOR SEQ ID NO: 55:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 55:

Cys Thr Arg Pro Asn Asn Asn Thr Arg Lys Gly Ile His Ile Gly Pro
1               5                   10                  15

Gly Arg Ala Phe Tyr Thr Thr Gly Asp Ile Ile Gly Asp Ile Arg Gln
            20                  25                  30

Ala His Cys
        35

(2) INFORMATION FOR SEQ ID NO: 56:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 56:

Cys Thr Arg Pro Asn Asn Asn Thr Arg Lys Asp Ile His Ile Gly Pro
1               5                   10                  15

Gly Arg Ala Phe Tyr Thr Thr Gly Asp Ile Ile Gly Asp Ile Arg Gln
            20                  25                  30

Ala His Cys
        35

(2) INFORMATION FOR SEQ ID NO: 57:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 57:

Cys Thr Arg Pro Asn Asn Asn Thr Arg Lys Glu Ile His Ile Gly Leu
1               5                   10                  15

Gly Arg Arg Phe Tyr Thr Thr Arg Lys Ile Ile Gly Asp Ile Arg Gln
            20                  25                  30

Ala His Cys
        35

(2) INFORMATION FOR SEQ ID NO: 58:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 58:

Cys Thr Arg Pro Asn Asn Asn Thr Arg Lys Glu Ile His Ile Gly Leu
1               5                   10                  15

Gly Arg Arg Phe Tyr Thr Thr Arg Lys Ile Ile Gly Asp Ile Arg Gln
            20                  25                  30

Ala His Cys
        35

(2) INFORMATION FOR SEQ ID NO: 59:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 59:

Cys Thr Arg Pro Asn Asn Asn Thr Arg Lys Gly Ile His Ile Gly Pro
1               5                   10                  15

Gly Arg Ala Phe Tyr Ala Thr Gly Glu Ile Ile Gly Asp Ile Arg Gln
            20                  25                  30

Ala His Cys
        35

(2) INFORMATION FOR SEQ ID NO: 60:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 60:

```
Cys Thr Arg Pro Asn Asn Asn Thr Arg Lys Gly Ile His Ile Gly Pro
1               5                   10                  15
Gly Arg Ala Phe Tyr Ala Thr Gly Asp Ile Ile Gly Asp Ile Arg Gln
            20                  25                  30
Ala His Cys
        35
```

(2) INFORMATION FOR SEQ ID NO: 61:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 61:

```
Cys Thr Arg Pro Asn Asn Asn Thr Arg Lys Gly Ile His Ile Gly Pro
1               5                   10                  15
Gly Gly Ala Phe Tyr Ala Thr Gly Asp Ile Ile Gly Asp Ile Arg Gln
            20                  25                  30
Ala His Cys
        35
```

(2) INFORMATION FOR SEQ ID NO: 62:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 62:

```
Cys Thr Arg Pro Asn Asn Asn Thr Arg Lys Gly Ile His Ile Gly Pro
1               5                   10                  15
Gly Gly Ala Phe Tyr Ala Thr Gly Asp Ile Ile Gly Asp Ile Ile Gln
            20                  25                  30
Ala His Cys
        35
```

(2) INFORMATION FOR SEQ ID NO: 63:

(i) SEQUENCE CHARACTERISTICS:
        (A) LENGTH: 34 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 63:

Cys Thr Arg Pro Asn Asn Asn Thr Arg Arg Asp Ile His Ile Gly Leu
1               5                   10                  15

Gly Arg Arg Phe Tyr Thr Arg Lys Ile Ile Gly Asp Ile Arg Gln Ala
            20                  25                  30

His Cys (2) INFORMATION FOR SEQ ID NO: 64:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 64:

Cys Thr Arg Pro Asn Asn Asn Thr Arg Lys Ser Ile His Ile Gly Pro
1               5                   10                  15

Gly Arg Ala Phe Tyr Ala Thr Gly Glu Ile Ile Gly Asp Ile Arg Gln
            20                  25                  30

Ala His Cys
        35

(2) INFORMATION FOR SEQ ID NO: 65:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 65:

Cys Thr Arg Pro Asn Asn Asn Thr Arg Lys Ser Ile His Ile Gly Pro
1               5                   10                  15

Gly Arg Ala Phe Tyr Ala Thr Gly Glu Ile Ile Gly Asp Ile Arg Gln
            20                  25                  30

Ala His Cys
        35

(2) INFORMATION FOR SEQ ID NO: 66:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 66:

Cys Thr Arg Pro Gly Asn Asn Thr Arg Lys Ser Ile Asn Ile Gly Pro

```
1               5                  10                 15
Gly Arg Ala Phe Tyr Ala Thr Gly Ala Ile Ile Gly Asp Ile Arg Gln
            20                 25                 30
Ala His Cys
        35

(2) INFORMATION FOR SEQ ID NO: 67:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 67:

Cys Thr Arg Pro Asn Asn Asn Thr Arg Lys Ser Ile Tyr Ile Gly Pro
1               5                  10                 15
Gly Arg Ala Phe Tyr Ala Thr Gly Glu Ile Ile Gly Asp Ile Arg Gln
            20                 25                 30
Ala His Cys
        35

(2) INFORMATION FOR SEQ ID NO: 68:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 68:

Cys Thr Arg Pro Asn Asn Asn Thr Arg Lys Ser Ile Tyr Ile Gly Pro
1               5                  10                 15
Gly Arg Ala Phe Tyr Ala Thr Gly Glu Ile Ile Gly Asp Ile Ile Gln
            20                 25                 30
Ala His Cys
        35

(2) INFORMATION FOR SEQ ID NO: 69:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 69:

Cys Thr Arg Pro Asn Asn Asn Thr Arg Lys Ser Ile Pro Ile Gly Pro
1               5                  10                 15
Gly Arg Ala Phe Tyr Thr Thr Gly Glu Ile Ile Gly Asp Ile Arg Gln
            20                 25                 30
Ala His Cys
        35
```

(2) INFORMATION FOR SEQ ID NO: 70:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 70:

```
Cys Thr Arg Pro Asn Asn Asn Thr Arg Arg Ser Ile Thr Ile Gly Pro
1               5                   10                  15

Gly Arg Ala Phe Tyr Thr Thr Gly Glu Ile Ile Gly Asn Ile Arg Gln
            20                  25                  30

Ala His Cys
        35
```

(2) INFORMATION FOR SEQ ID NO: 71:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 71:

```
Cys Thr Arg Pro Asn Asn Asn Thr Arg Lys Ser Ile Asn Ile Gly Pro
1               5                   10                  15

Gly Arg Ala Phe Tyr Thr Thr Gly Glu Ile Ile Gly Asp Ile Arg Gln
            20                  25                  30

Ala His Cys
        35
```

(2) INFORMATION FOR SEQ ID NO: 72:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 72:

```
Cys Thr Arg Pro Asn Asn Asn Thr Arg Lys Ser Ile Thr Ile Gly Pro
1               5                   10                  15

Gly Arg Ala Phe Tyr Thr Thr Gly Glu Ile Ile Gly Asn Ile Arg Gln
            20                  25                  30

Ala His Cys
        35
```

(2) INFORMATION FOR SEQ ID NO: 73:

(i) SEQUENCE CHARACTERISTICS:
        (A) LENGTH: 35 amino acids
        (B) TYPE: amino acid (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 73:

Cys Thr Arg Pro Asn Asn Asn Thr Arg Lys Ser Ile Asn Met Gly Pro
1               5                   10                  15

Gly Arg Ala Ile Tyr Thr Thr Gly Gln Ile Val Gly Asp Ile Arg Gln
            20                  25                  30

Ala His Cys
        35

(2) INFORMATION FOR SEQ ID NO: 74:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 74:

Cys Thr Arg Pro Asn Asn Asn Thr Arg Lys Gly Ile His Met Gly Pro
1               5                   10                  15

Gly Arg Ala Phe Tyr Ala Thr Gly Asp Ile Ile Gly Asp Ile Arg Gln
            20                  25                  30

Ala His Cys
        35

(2) INFORMATION FOR SEQ ID NO: 75:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 75:

Cys Thr Arg Pro Asn Asn Asn Thr Arg Lys Ser Ile His Ile Gly Pro
1               5                   10                  15

Gly Arg Ala Phe Tyr Ala Thr Gly Asp Ile Ile Gly Asp Ile Arg Gln
            20                  25                  30

Ala His Cys
        35

(2) INFORMATION FOR SEQ ID NO: 76:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO

```
            (xi) SEQUENCE DESCRIPTION: SEQ ID NO: 76:

Cys Thr Arg Pro Asn Asn Asn Thr Arg Lys Arg Ile His Ile Gly Pro
1               5                  10                  15

Gly Arg Ala Phe Tyr Thr Thr Gly Gln Ile Ile Gly Asn Ile Arg Gln
            20                  25                  30

Ala His Cys
        35

(2) INFORMATION FOR SEQ ID NO: 77:

(i) SEQUENCE CHARACTERISTICS:
           (A) LENGTH: 35 amino acids
           (B) TYPE: amino acid
           (C) STRANDEDNESS: unknown
           (D) TOPOLOGY: circular (ii) MOLECULE TYPE: peptide (iii) HYPOTHETICAL: NO (xi) SEQUENCE DESCRIPTION: SEQ ID NO: 77:

Cys Thr Arg Pro Asn Asn Asn Thr Arg Lys Ser Ile Pro Ile Gly Pro
1               5                  10                  15

Gly Arg Ala Phe Tyr Leu Ala Gly Ala Ile Ile Gly Asp Ile Arg Gln
            20                  25                  30

Ala His Cys
        35

(2) INFORMATION FOR SEQ ID NO: 78:

(i) SEQUENCE CHARACTERISTICS:
           (A) LENGTH: 35 amino acids
           (B) TYPE: amino acid
           (C) STRANDEDNESS: unknown
           (D) TOPOLOGY: circular (ii) MOLECULE TYPE: peptide (iii) HYPOTHETICAL: NO (xi) SEQUENCE DESCRIPTION: SEQ ID NO: 78:

Cys Thr Arg Pro Asn Asn Asn Thr Arg Lys Ser Ile His Ile Gly Pro
1               5                  10                  15

Gly Arg Ala Phe Tyr Ala Pro Gly Glu Ile Ile Gly Asp Ile Arg Gln
            20                  25                  30

Ala His Cys
        35

(2) INFORMATION FOR SEQ ID NO: 79:

(i) SEQUENCE CHARACTERISTICS:
           (A) LENGTH: 35 amino acids
           (B) TYPE: amino acid
           (C) STRANDEDNESS: unknown
           (D) TOPOLOGY: circular (ii) MOLECULE TYPE: peptide (iii) HYPOTHETICAL: NO (xi) SEQUENCE DESCRIPTION: SEQ ID NO: 79:

Cys Thr Arg Pro Asn Asn Asn Thr Arg Lys Ser Ile Asn Ile Gly Pro
1               5                  10                  15

Gly Arg Ala Phe Tyr Ala Thr Gly Ala Ile Ile Gly Asp Ile Arg Arg
            20                  25                  30
```

Ala His Cys
    35

(2) INFORMATION FOR SEQ ID NO: 80:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 80:

Cys Thr Arg Leu Ser Ala Asn Lys Ile Arg His Met His Ile Gly Pro
1               5                   10                  15

Gly Arg Ala Phe Tyr Ala Thr Gly Lys Ile Ile Gly Asp Ile Arg Lys
            20                  25                  30

Ala His Cys
    35

(2) INFORMATION FOR SEQ ID NO: 81:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 81:

Cys Ile Arg Pro Gly Asn Asn Thr Arg Lys Ser Ile Pro Ile Gly Pro
1               5                   10                  15

Gly Arg Ala Phe Tyr Ala Thr Gly Asp Ile Ile Gly Asp Ile Arg Gln
            20                  25                  30

Ala His Cys
    35

(2) INFORMATION FOR SEQ ID NO: 82:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 82:

Cys Thr Arg Pro Asn Asn Asn Thr Arg Lys Gly Ile His Ile Gly Pro
1               5                   10                  15

Gly Arg Ala Phe Tyr Ala Ala Gly Ala Ile Ile Gly Asp Ile Arg Gln
            20                  25                  30

Ala His Cys
    35

(2) INFORMATION FOR SEQ ID NO: 83:

(i) SEQUENCE CHARACTERISTICS:
    (A) LENGTH: 35 amino acids
    (B) TYPE: amino acid
    (C) STRANDEDNESS: unknown
    (D) TOPOLOGY: circular (ii) MOLECULE TYPE: peptide (iii) HYPOTHETICAL: NO (xi) SEQUENCE DESCRIPTION: SEQ ID NO: 83:

Cys Thr Arg Pro Asn Asn Asn Thr Arg Lys Gly Ile His Leu Gly Pro
1               5                   10                  15

Gly Arg Ala Trp Phe Thr Thr Gly Glu Ile Ile Gly Asp Ile Arg Lys
            20                  25                  30

Ala His Cys
        35

(2) INFORMATION FOR SEQ ID NO: 84:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 84:

Cys Thr Arg Pro Asn Asn Asn Thr Arg Lys Gly Ile His Leu Gly Pro
1               5                   10                  15

Gly Arg Ala Trp Phe Ala Thr Gly Glu Ile Ile Gly Asp Ile Arg Lys
            20                  25                  30

Ala His Cys
        35

(2) INFORMATION FOR SEQ ID NO: 85:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 85:

Cys Thr Arg Pro Asn Asn Tyr Thr Arg Lys Gly Ile His Leu Gly Pro
1               5                   10                  15

Gly Arg Ala Trp Leu Thr Thr Arg Lys Ile Ile Gly Asp Ile Arg Lys
            20                  25                  30

Ala His Cys
        35

(2) INFORMATION FOR SEQ ID NO: 86:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 86:

Cys Thr Arg Pro Ser Asn Asn Thr Arg Lys Ser Ile His Ile Gly Pro
1               5                   10                  15

Gly Arg Ala Phe Tyr Ala Thr Gly Asp Ile Ile Gly Asp Ile Arg Gln
            20                  25                  30

Ala His Cys
        35

(2) INFORMATION FOR SEQ ID NO: 87:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 87:

Cys Thr Arg Pro Asn Asn Asn Thr Arg Lys Gly Ile His Ile Gly Pro
1               5                   10                  15

Gly Lys Ala Phe Tyr Ala Thr Gly Gln Ile Ile Gly Asp Ile Arg Gln
            20                  25                  30

Ala His Cys
        35

(2) INFORMATION FOR SEQ ID NO: 88:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 88:

Cys Thr Arg Pro Asn Asn Asn Thr Arg Lys Gly Ile His Met Gly Pro
1               5                   10                  15

Gly Lys Ala Phe Tyr Ala Thr Gly Gln Ile Ile Gly Asp Ile Arg Gln
            20                  25                  30

Ala His Cys
        35

(2) INFORMATION FOR SEQ ID NO: 89:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 89:

Cys Thr Arg Pro Asn Asn Asn Thr Arg Lys Gly Ile His Ile Gly Pro
1               5                   10                  15

Gly Arg Ala Phe Tyr Ala Ala Arg Lys Ile Ile Gly Asp Ile Arg Gln
            20                  25                  30

Ala His Cys
        35

(2) INFORMATION FOR SEQ ID NO: 90:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 90:

Cys Thr Arg Pro Asn Asn Asn Thr Arg Arg Ser Ile His Ile Gly Pro
1               5                   10                  15

Gly Arg Ala Phe Trp Ala Thr Gly Asp Ile Ile Gly Asp Ile Arg Gln
            20                  25                  30

Ala His Cys
        35

(2) INFORMATION FOR SEQ ID NO: 91:

(i) SEQUENCE CHARACTERISTICS:
        (A) LENGTH: 36 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 91:

Cys Thr Arg Pro Asn Asn Asn Ile Arg Arg Met Ile His Ile Gly
1               5                   10                  15

Pro Gly Arg Ala Phe Tyr Thr Thr Gly Glu Ile Ile Gly Asn Ile Arg
                20                  25                  30

Gln Ala His Cys
        35

(2) INFORMATION FOR SEQ ID NO: 92:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 92:

Cys Thr Arg Pro Asn Asn Asn Thr Arg Lys Ser Ile His Ile Gly Pro
1               5                   10                  15

Gly Arg Ala Phe Tyr Thr Thr Gly Glu Ile Ile Gly Asn Ile Arg Gln
            20                  25                  30

Ala His Cys
        35

(2) INFORMATION FOR SEQ ID NO: 93:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 93:

```
Cys Thr Arg Pro Asn Asn Asn Thr Arg Lys Ser Ile Ser Ile Gly Pro
1               5                   10                  15

Gly Arg Ala Phe Tyr Thr Thr Gly Glu Ile Ile Gly Asn Ile Arg Gln
            20                  25                  30

Ala His Cys
        35
```

(2) INFORMATION FOR SEQ ID NO: 94:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 94:

```
Cys Thr Arg Pro Asn Asn Asn Thr Arg Lys Arg Ile Ser Leu Ser Pro
1               5                   10                  15

Gly Arg Val Phe Tyr Thr Thr Gly Glu Ile Arg Gly Asp Ile Arg Gln
            20                  25                  30

Ala His Cys
        35
```

(2) INFORMATION FOR SEQ ID NO: 95:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 95:

```
Cys Thr Arg Pro Asn Asn Asn Thr Arg Lys Ser Ile Ser Ile Gly Pro
1               5                   10                  15

Gly Arg Ala Phe Tyr Thr Thr Gly Glu Ile Ile Gly Asp Ile Ile Gln
            20                  25                  30

Ala His Cys
        35
```

(2) INFORMATION FOR SEQ ID NO: 96:

(i) SEQUENCE CHARACTERISTICS:
        (A) LENGTH: 35 amino acids
        (B) TYPE: amino acid
        (C) STRANDEDNESS: unknown (D) TOPOLOGY: circular (ii) MOLECULE TYPE: peptide (iii) HYPOTHETICAL: NO (xi) SEQUENCE DESCRIPTION: SEQ ID NO: 96:

Cys Thr Arg Pro Asn Asn Asn Val Arg Lys Arg Ile Ser Leu Ser Pro
1               5                  10                  15

Gly Arg Val Phe Tyr Thr Thr Gly Glu Ile Ile Gly Asp Ile Arg Lys
            20                  25                  30

Ala His Cys
        35

(2) INFORMATION FOR SEQ ID NO: 97:

(i) SEQUENCE CHARACTERISTICS:
          (A) LENGTH: 35 amino acids
          (B) TYPE: amino acid
          (C) STRANDEDNESS: unknown
          (D) TOPOLOGY: circular (ii) MOLECULE TYPE: peptide (iii) HYPOTHETICAL: NO (xi) SEQUENCE DESCRIPTION: SEQ ID NO: 97:

Cys Thr Arg Pro Asn Asn Asn Ile Arg Lys Arg Ile Ser Leu Ser Pro
1               5                  10                  15

Gly Arg Val Tyr Tyr Thr Thr Gly Glu Ile Arg Gly Asp Ile Arg Lys
            20                  25                  30

Ala Tyr Cys
        35

(2) INFORMATION FOR SEQ ID NO: 98:

(i) SEQUENCE CHARACTERISTICS:
          (A) LENGTH: 35 amino acids
          (B) TYPE: amino acid
          (C) STRANDEDNESS: unknown
          (D) TOPOLOGY: circular (ii) MOLECULE TYPE: peptide (iii) HYPOTHETICAL: NO (xi) SEQUENCE DESCRIPTION: SEQ ID NO: 98:

Cys Thr Arg Pro Asn Asn Asn Val Arg Lys Arg Ile Ser Leu Ser Pro
1               5                  10                  15

Gly Arg Val Tyr Tyr Thr Thr Gly Glu Ile Arg Gly Asp Ile Arg Lys
            20                  25                  30

Ala Tyr Cys
        35

(2) INFORMATION FOR SEQ ID NO: 99:

(i) SEQUENCE CHARACTERISTICS:
          (A) LENGTH: 35 amino acids
          (B) TYPE: amino acid
          (C) STRANDEDNESS: unknown
          (D) TOPOLOGY: circular (ii) MOLECULE TYPE: peptide (iii) HYPOTHETICAL: NO (xi) SEQUENCE DESCRIPTION: SEQ ID NO: 99:

Cys Thr Arg Phe Asn Asn Asn Thr Arg Lys Arg Ile Ser Leu Ser Pro
1               5                   10                  15

Gly Arg Val Phe Tyr Thr Thr Gly Glu Ile Ile Gly Asp Ile Arg Arg
            20                  25                  30

Ala His Cys
        35

(2) INFORMATION FOR SEQ ID NO: 100:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 100:

Cys Thr Arg Pro Asn Asn Asn Thr Arg Lys Ser Ile Ser Ile Gly Pro
1               5                   10                  15

Gly Arg Ala Phe Tyr Ala Thr Gly Asp Ile Ile Gly Asp Ile Arg Gln
            20                  25                  30

Ala His Cys
        35

(2) INFORMATION FOR SEQ ID NO: 101:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 101:

Cys Thr Arg Pro Asn Asn Asn Thr Arg Lys Arg Ile Ser Leu Ser Pro
1               5                   10                  15

Gly Arg Val Phe Tyr Thr Thr Gly Glu Ile Ile Gly Asp Ile Arg Arg
            20                  25                  30

Ala His Cys
        35

(2) INFORMATION FOR SEQ ID NO: 102:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 102:

Cys Thr Arg Pro Asn Asn Asn Ile Arg Lys Arg Ile Ser Leu Ser Pro
1               5                   10                  15

Gly Arg Val Phe Tyr Thr Thr Gly Glu Ile Ile Gly Asp Ile Arg Lys
            20                  25                  30

Ala His Cys
    35

(2) INFORMATION FOR SEQ ID NO: 103:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 103:

Cys Thr Arg Pro Asn Asn Asn Thr Arg Lys Ser Ile Ser Met Gly Pro
1               5                   10                  15

Gly Lys Ala Phe Tyr Thr Thr Gly Ala Ile Ile Gly Asn Ile Arg Gln
            20                  25                  30

Ala His Cys
    35

(2) INFORMATION FOR SEQ ID NO: 104:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 104:

Cys Thr Arg Pro His Asn Asn Thr Arg Lys Ser Ile Asn Ile Gly Pro
1               5                   10                  15

Gly Arg Ala Phe Tyr Thr Thr Gly Glu Ile Ile Gly Asp Ile Arg Gln
            20                  25                  30

Ala His Cys
    35

(2) INFORMATION FOR SEQ ID NO: 105:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 105:

Cys Thr Arg Pro Asn Asn Asn Thr Arg Lys Ser Ile His Ile Gly Pro
1               5                   10                  15

Gly Arg Ala Phe Tyr Thr Thr Gly Glu Ile Ile Gly Asp Ile Arg Gln
            20                  25                  30

Ala His Cys
    35

(2) INFORMATION FOR SEQ ID NO: 106:

(i) SEQUENCE CHARACTERISTICS:

(A) LENGTH: 35 amino acids
          (B) TYPE: amino acid
          (C) STRANDEDNESS: unknown
          (D) TOPOLOGY: circular (ii) MOLECULE TYPE: peptide (iii) HYPOTHETICAL: NO (xi) SEQUENCE DESCRIPTION: SEQ ID NO: 106:

Cys Thr Arg Pro Asn Asn Asn Thr Arg Lys Gly Ile Asn Ile Gly Pro
1               5                   10                  15

Gly Arg Ala Phe Tyr Ala Thr Gly Gln Ile Ile Gly Asn Ile Arg Gln
            20                  25                  30

Ala His Cys
        35

(2) INFORMATION FOR SEQ ID NO: 107:

(i) SEQUENCE CHARACTERISTICS:
          (A) LENGTH: 35 amino acids
          (B) TYPE: amino acid
          (C) STRANDEDNESS: unknown
          (D) TOPOLOGY: circular (ii) MOLECULE TYPE: peptide (iii) HYPOTHETICAL: NO (xi) SEQUENCE DESCRIPTION: SEQ ID NO: 107:

Cys Thr Arg Pro Asn Asn Asn Thr Arg Gln Gly Ile His Tyr Gly Pro
1               5                   10                  15

Gly Arg Ala Phe Tyr Thr Thr Arg Arg Ile Ile Gly Asp Ile Arg Gln
            20                  25                  30

Ala His Cys
        35

(2) INFORMATION FOR SEQ ID NO: 108:

(i) SEQUENCE CHARACTERISTICS:
          (A) LENGTH: 35 amino acids
          (B) TYPE: amino acid
          (C) STRANDEDNESS: unknown
          (D) TOPOLOGY: circular (ii) MOLECULE TYPE: peptide (iii) HYPOTHETICAL: NO (xi) SEQUENCE DESCRIPTION: SEQ ID NO: 108:

Cys Thr Arg Pro Asn Asn Asn Thr Arg Lys Gly Ile His Ile Gly Pro
1               5                   10                  15

Gly Arg Ala Phe Tyr Thr Thr Arg Arg Ile Ile Gly Asp Ile Arg Gln
            20                  25                  30

Ala His Cys
        35

(2) INFORMATION FOR SEQ ID NO: 109:

(i) SEQUENCE CHARACTERISTICS:
          (A) LENGTH: 34 amino acids
          (B) TYPE: amino acid
          (C) STRANDEDNESS: unknown
          (D) TOPOLOGY: circular (ii) MOLECULE TYPE: peptide (iii) HYPOTHETICAL: NO (xi) SEQUENCE DESCRIPTION: SEQ ID NO: 109:

Cys Thr Arg Pro Gly Asn Asn Thr Lys Arg Ser Ile Pro Ile Gly Pro
1               5                   10                  15

Gly Lys Val Phe Phe Thr Thr Glu Ile Ile Gly Asp Ile Arg Gln Ala
            20                  25                  30

His Cys (2) INFORMATION FOR SEQ ID NO: 110:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 110:

Cys Thr Arg Pro Gly Asn Asn Thr Lys Arg Ser Ile Tyr Ile Gly Pro
1               5                   10                  15

Gly Arg Ala Phe His Thr Thr Asp Arg Ile Ile Gly Asp Ile Arg Arg
            20                  25                  30

Ala His Cys
        35

(2) INFORMATION FOR SEQ ID NO: 111:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 111:

Cys Thr Arg Pro Gly Asn Asn Thr Lys Arg Ser Ile Tyr Ile Gly Pro
1               5                   10                  15

Gly Arg Ala Phe His Thr Thr Asp Arg Ile Ile Gly Asp Ile Arg Gln
            20                  25                  30

Ala His Cys
        35

(2) INFORMATION FOR SEQ ID NO: 112:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 112:

Cys Thr Arg Pro Gly Asn Asn Thr Lys Arg Ser Ile Tyr Ile Gly Pro
1               5                   10                  15

Gly Arg Ala Phe Gln Thr Thr Asp Arg Ile Ile Gly Asp Ile Arg Arg

```
                    20                  25                  30
Ala His Cys
        35

(2) INFORMATION FOR SEQ ID NO: 113:

(i) SEQUENCE CHARACTERISTICS:
        (A) LENGTH: 34 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 113:

Cys Thr Arg Pro Gly Asn Asn Thr Arg Arg Ser Ile Pro Ile Gly Pro
1               5                   10                  15

Gly Lys Ala Phe Phe Thr Thr Gln Ile Ile Gly Asp Ile Arg Gln Ala
            20                  25                  30

His Cys (2) INFORMATION FOR SEQ ID NO: 114:

(i) SEQUENCE CHARACTERISTICS:
        (A) LENGTH: 34 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 114:

Cys Thr Arg Pro Gly Asn Asn Thr Lys Arg Ser Ile Pro Ile Gly Pro
1               5                   10                  15

Gly Lys Ala Phe Phe Thr Thr Glu Ile Ile Gly Asp Ile Arg Gln Ala
            20                  25                  30

His Cys (2) INFORMATION FOR SEQ ID NO: 115:

(i) SEQUENCE CHARACTERISTICS:
        (A) LENGTH: 34 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 115:

Cys Thr Arg Pro Gly Asn Asn Thr Arg Arg Ser Ile Pro Ile Gly Pro
1               5                   10                  15

Gly Lys Val Phe Phe Thr Thr Glu Ile Ile Gly Asp Ile Arg Gln Ala
            20                  25                  30

His Cys (2) INFORMATION FOR SEQ ID NO: 116:

(i) SEQUENCE CHARACTERISTICS:
        (A) LENGTH: 35 amino acids
```

(B) TYPE: amino acid
            (C) STRANDEDNESS: unknown
            (D) TOPOLOGY: circular (ii) MOLECULE TYPE: peptide (iii) HYPOTHETICAL: NO (xi) SEQUENCE DESCRIPTION: SEQ ID NO: 116:

Cys Thr Arg Pro Gly Asn Asn Thr Lys Arg Ser Ile Tyr Ile Gly Pro
1               5                   10                  15

Gly Arg Ala Phe His Thr Thr Asp Arg Ile Ile Gly Asp Ile Arg Lys
            20                  25                  30

Ala His Cys
        35

(2) INFORMATION FOR SEQ ID NO: 117:

(i) SEQUENCE CHARACTERISTICS:
        (A) LENGTH: 34 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 117:

Cys Thr Arg Pro Gly Asn Asn Thr Arg Arg Ser Ile Pro Ile Gly Pro
1               5                   10                  15

Gly Lys Ala Phe Phe Thr Thr Glu Ile Ile Gly Asp Ile Arg Gln Ala
            20                  25                  30

His Cys (2) INFORMATION FOR SEQ ID NO: 118:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 118:

Cys Thr Arg Pro Asn Asn Asn Thr Arg Lys Ser Ile Pro Ile Gly Pro
1               5                   10                  15

Gly Arg Ala Phe Tyr Ala Thr Gly Glu Ile Ile Gly Asp Ile Arg Gln
            20                  25                  30

Ala His Cys
        35

(2) INFORMATION FOR SEQ ID NO: 119:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 119:

Cys Thr Arg Pro Asn Asn Asn Thr Arg Lys Ser Ile Pro Ile Gly Pro
1               5                   10                  15

Gly Arg Ala Phe Tyr Thr Thr Gly Asp Ile Ile Gly Asp Ile Arg Gln
            20                  25                  30

Ala His Cys
        35

(2) INFORMATION FOR SEQ ID NO: 120:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 120:

Cys Ile Arg Pro Asn Asn Asn Thr Arg Lys Ser Ile Pro Ile Gly Pro
1               5                   10                  15

Gly Arg Ala Phe Tyr Thr Thr Gly Glu Ile Ile Gly Asp Ile Arg Gln
            20                  25                  30

Ala His Cys
        35

(2) INFORMATION FOR SEQ ID NO: 121:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 121:

Cys Thr Arg Pro Asn Asn Asn Thr Arg Lys Ser Ile Pro Ile Gly Pro
1               5                   10                  15

Gly Arg Ala Phe Tyr Ala Thr Gly Asp Ile Ile Gly Asp Ile Arg Gln
            20                  25                  30

Ala His Cys
        35

(2) INFORMATION FOR SEQ ID NO: 122:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 122:

Cys Thr Arg Pro Asn Asn Asn Thr Arg Lys Ser Ile His Ile Ala Pro
1               5                   10                  15

Gly Arg Ala Phe Tyr Ala Thr Gly Asp Ile Ile Gly Asp Ile Arg Gln
            20                  25                  30

Ala His Cys
    35

(2) INFORMATION FOR SEQ ID NO: 123:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 123:

Cys Thr Arg Pro Asn Asn Asn Thr Arg Arg Ser Ile Thr Ile Gly Pro
1               5                   10                  15

Gly Arg Ala Phe Tyr Ala Thr Gly Glu Ile Thr Gly Asp Ile Arg Gln
            20                  25                  30

Ala His Cys
    35

(2) INFORMATION FOR SEQ ID NO: 124:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 124:

Cys Thr Arg Pro Asn Asn Asn Thr Arg Lys Ser Ile Thr Ile Gly Pro
1               5                   10                  15

Gly Arg Ala Phe Tyr Thr Thr Gly Glu Ile Ile Gly Asp Ile Arg Gln
            20                  25                  30

Ala His Cys
    35

(2) INFORMATION FOR SEQ ID NO: 125:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 125:

Cys Thr Arg Pro Asn Asn Asn Thr Arg Lys Ser Ile Thr Ile Gly Pro
1               5                   10                  15

Gly Arg Ala Phe Tyr Thr Thr Gly Asp Ile Ile Gly Asp Ile Arg Gln
            20                  25                  30

Ala His Cys
    35

(2) INFORMATION FOR SEQ ID NO: 126:

(i) SEQUENCE CHARACTERISTICS:
    (A) LENGTH: 35 amino acids
    (B) TYPE: amino acid
    (C) STRANDEDNESS: unknown
    (D) TOPOLOGY: circular (ii) MOLECULE TYPE: peptide (iii) HYPOTHETICAL: NO (xi) SEQUENCE DESCRIPTION: SEQ ID NO: 126:

Cys Val Arg Pro Asn Asn Asn Thr Arg Lys Ser Ile Tyr Ile Gly Pro
1               5                   10                  15

Gly Arg Ala Phe Tyr Ala Thr Gly Asp Ile Ile Gly Asn Ile Arg Gln
            20                  25                  30

Ala His Cys
        35

(2) INFORMATION FOR SEQ ID NO: 127:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 127:

Cys Val Arg Pro Asn Asn Asn Thr Arg Lys Ser Ile Ser Ile Gly Pro
1               5                   10                  15

Gly Arg Ala Phe Tyr Ala Thr Gly Asp Ile Ile Gly Asn Ile Arg Gln
            20                  25                  30

Ala His Cys
        35

(2) INFORMATION FOR SEQ ID NO: 128:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 128:

Cys Val Arg Pro Asn Asn Asn Thr Arg Lys Ser Ile Tyr Ile Gly Pro
1               5                   10                  15

Gly Arg Ala Phe Tyr Ala Ile Gly Asp Ile Ile Gly Asn Ile Arg Gln
            20                  25                  30

Ala His Cys
        35

(2) INFORMATION FOR SEQ ID NO: 129:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 129:

Cys Val Arg Pro Asn Asn Asn Thr Arg Lys Ser Ile Pro Ile Gly Pro
1               5                   10                  15

Gly Arg Ala Phe Tyr Ala Thr Gly Asp Ile Ile Gly Asn Ile Arg Gln
            20                  25                  30

Ala His Cys
        35

(2) INFORMATION FOR SEQ ID NO: 130:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 130:

Cys Val Arg Pro Asn Asn Asn Thr Arg Lys Ser Ile Tyr Ile Gly Pro
1               5                   10                  15

Gly Arg Ala Phe Tyr Ala Thr Gly Lys Arg Ile Gly Asn Ile Arg Gln
            20                  25                  30

Ala His Cys
        35

(2) INFORMATION FOR SEQ ID NO: 131:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 131:

Cys Thr Arg Pro Asn Asn Asn Thr Arg Arg Ser Ile Asn Ile Gly Pro
1               5                   10                  15

Gly Arg Ala Phe Phe Ala Thr Gly Asp Ile Ile Gly Asp Ile Arg Gln
            20                  25                  30

Ala His Cys
        35

(2) INFORMATION FOR SEQ ID NO: 132:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 132:

Cys Thr Arg Pro Asn Asn Asn Thr Arg Lys Ser Ile Asn Ile Gly Pro
1               5                   10                  15

Gly Arg Ala Phe Tyr Ala Thr Gly Glu Ile Ile Gly Asp Ile Arg Gln
            20                  25                  30

Ala His Cys
        35

(2) INFORMATION FOR SEQ ID NO: 133:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 133:

Cys Thr Arg Pro Asn Asn Asn Thr Arg Lys Ser Ile Asn Ile Gly Pro
1               5                   10                  15

Gly Arg Ala Phe Phe Thr Thr Gly Glu Ile Ile Gly Asp Ile Arg Gln
            20                  25                  30

Ala His Cys
        35

(2) INFORMATION FOR SEQ ID NO: 134:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 134:

Cys Thr Arg Pro Asn Asn Asn Thr Arg Lys Ser Ile Asn Ile Gly Pro
1               5                   10                  15

Gly Arg Ala Phe Tyr Ala Thr Gly Ala Ile Ile Gly Asp Ile Arg Gln
            20                  25                  30

Ala His Cys
        35

(2) INFORMATION FOR SEQ ID NO: 135:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 135:

Cys Thr Arg Pro Asn Asn Asn Thr Arg Lys Ser Ile His Ile Ala Pro
1               5                   10                  15

Gly Arg Ala Phe Tyr Ala Thr Gly Glu Ile Ile Gly Asp Ile Arg Gln
            20                  25                  30

Ala His Cys
        35

(2) INFORMATION FOR SEQ ID NO: 136:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 136:

```
Cys Thr Arg Pro Asn Asn Asn Thr Arg Lys Ser Ile His Ile Gly Pro
1               5                  10                 15
Gly Arg Ala Trp Tyr Thr Thr Gly Glu Val Ile Gly Asn Ile Arg Gln
            20                  25                 30
Ala His Cys
        35
```

(2) INFORMATION FOR SEQ ID NO: 137:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 137:

```
Cys Thr Arg Pro Asn Asn Asn Thr Arg Lys Ser Ile Asn Ile Gly Pro
1               5                  10                 15
Gly Arg Ala Trp Tyr Thr Thr Gly Glu Ile Ile Gly Asp Ile Arg Gln
            20                  25                 30
Ala His Cys
        35
```

(2) INFORMATION FOR SEQ ID NO: 138:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 138:

```
Cys Thr Arg Pro Asn Asn Asn Thr Arg Lys Arg Val Thr Met Gly Pro
1               5                  10                 15
Gly Arg Val Trp Tyr Thr Thr Gly Val Ile Ile Gly Asn Ile Arg Gln
            20                  25                 30
Ala His Cys
        35
```

(2) INFORMATION FOR SEQ ID NO: 139:

(i) SEQUENCE CHARACTERISTICS:
        (A) LENGTH: 35 amino acids
        (B) TYPE: amino acid
        (C) STRANDEDNESS: unknown (D) TOPOLOGY: circular (ii) MOLECULE TYPE: peptide (iii) HYPOTHETICAL: NO (xi) SEQUENCE DESCRIPTION: SEQ ID NO: 139:

Cys Thr Arg Pro Asn Asn Asn Thr Arg Lys Ser Ile His Ile Gly Pro
1               5                   10                  15

Gly Arg Ala Trp Tyr Thr Thr Gly Glu Ile Ile Gly Asn Ile Arg Gln
            20                  25                  30

Ala His Cys
        35

(2) INFORMATION FOR SEQ ID NO: 140:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 140:

Cys Thr Arg Pro Asn Asn Asn Thr Arg Lys Arg Val Thr Met Gly Pro
1               5                   10                  15

Gly Arg Ala Leu Tyr Thr Thr Gly Glu Ile Ile Gly Asp Ile Arg Gln
            20                  25                  30

Ala His Cys
        35

(2) INFORMATION FOR SEQ ID NO: 141:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 141:

Cys Thr Arg Pro Asn Asn Asn Thr Arg Lys Arg Val Thr Met Gly Pro
1               5                   10                  15

Gly Arg Val Trp Tyr Thr Thr Gly Glu Ile Ile Gly Asn Ile Arg Gln
            20                  25                  30

Ala His Cys
        35

(2) INFORMATION FOR SEQ ID NO: 142:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 142:

```
Cys Thr Arg Pro Asn Asn Asn Thr Arg Lys Arg Val Thr Met Gly Pro
1               5                   10                  15

Gly Arg Val Trp Tyr Thr Thr Gly Glu Ile Ile Gly Asn Ile Lys Gln
            20                  25                  30

Ala His Cys
        35

(2) INFORMATION FOR SEQ ID NO: 143:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 143:

Cys Thr Arg Pro Asn Asn Tyr Thr Arg Arg Leu Ser Ile Gly Pro
1               5                   10                  15

Gly Arg Ala Phe Arg Thr Ile Gly Gln Ile Ile Gly Asn Ile Arg Gln
            20                  25                  30

Ala His Cys
        35

(2) INFORMATION FOR SEQ ID NO: 144:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 144:

Cys Thr Arg Pro Asn Asn Asn Thr Arg Arg Arg Ile Arg Ile Gly Pro
1               5                   10                  15

Gly Arg Ala Phe Arg Thr Ile Gly Gln Ile Ile Gly Asn Ile Arg Gln
            20                  25                  30

Ala His Cys
        35

(2) INFORMATION FOR SEQ ID NO: 145:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 145:

Cys Thr Arg Pro Asn Asn Asn Ile Arg Arg Arg Ile Ser Ile Gly Pro
1               5                   10                  15

Gly Arg Ala Phe Arg Thr Ile Gly Gln Ile Ile Gly Asn Ile Arg Gln
            20                  25                  30
```

Ala His Cys
      35

(2) INFORMATION FOR SEQ ID NO: 146:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 146:

Cys Thr Arg Pro Asn Asn Asn Lys Arg Arg Arg Ile Ile Ile Gly Pro
1               5                   10                  15

Gly Arg Ala Phe Arg Thr Ile Gly Gln Ile Ile Gly Asn Ile Arg Gln
            20                  25                  30

Ala His Cys
      35

(2) INFORMATION FOR SEQ ID NO: 147:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 147:

Cys Thr Arg Pro Asn Asn Asn Thr Arg Arg Val Ser Ile Gly Pro
1               5                   10                  15

Gly Arg Ala Phe Arg Thr Ile Gly Gln Ile Ile Gly Asn Thr Arg Gln
            20                  25                  30

Ala His Cys
      35

(2) INFORMATION FOR SEQ ID NO: 148:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 148:

Cys Thr Arg Pro Asn Asn Tyr Thr Arg Arg Ile Ser Ile Gly Pro
1               5                   10                  15

Gly Arg Ala Phe Arg Thr Met Gly Gln Ile Ile Gly Asp Ile Arg Gln
            20                  25                  30

Ala His Cys
      35

(2) INFORMATION FOR SEQ ID NO: 149:

(i) SEQUENCE CHARACTERISTICS:

(A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 149:

Cys Thr Arg Pro Asn Asn Asn Thr Arg Arg Ile Ser Ile Gly Pro
1               5                   10                  15

Gly Arg Ala Phe Arg Thr Ile Gly Gln Ile Ile Gly Asn Ile Arg Gln
            20                  25                  30

Ala His Cys
        35

(2) INFORMATION FOR SEQ ID NO: 150:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 150:

Cys Thr Arg Pro Asn Asn Asn Thr Arg Lys Ser Ile His Ile Gly Pro
1               5                   10                  15

Gly Arg Ala Phe Tyr Thr Thr Gly Gly Ile Ile Gly Asp Ile Gln Gln
            20                  25                  30

Ala His Cys
        35

(2) INFORMATION FOR SEQ ID NO: 151:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 151:

Cys Thr Arg Pro Asn Asn Asn Thr Arg Lys Ser Ile His Ile Gly Pro
1               5                   10                  15

Gly Arg Ala Leu Tyr Thr Thr Gly Glu Ile Ile Gly Asp Ile Arg Gln
            20                  25                  30

Ala His Cys
        35

(2) INFORMATION FOR SEQ ID NO: 152:

(i) SEQUENCE CHARACTERISTICS:
        (A) LENGTH: 36 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 152:

Cys Thr Arg Pro Asn Asn Asn Thr Arg Lys Arg Ile Arg Ile Gln Arg
1               5                   10                  15

Gly Pro Gly Arg Ala Phe Val Thr Ile Gly Lys Ile Gly Asn Met Arg
            20                  25                  30

Gln Ala His Cys
        35

(2) INFORMATION FOR SEQ ID NO: 153:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 153:

Cys Thr Arg Pro Asn Asn Asn Thr Arg Lys Ser Ile Ser Ile Gly Pro
1               5                   10                  15

Gly Arg Ala Trp Tyr Thr Thr Gly Asp Ile Ile Gly Asp Ile Arg Gln
            20                  25                  30

Ala His Cys
        35

(2) INFORMATION FOR SEQ ID NO: 154:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 154:

Cys Thr Arg Pro Asn Asn Asn Thr Arg Lys Ser Ile Ser Lys Gly Pro
1               5                   10                  15

Gly Arg Ala Trp Tyr Thr Thr Gly Asp Ile Ile Gly Asp Ile Arg Gln
            20                  25                  30

Ala His Cys
        35

(2) INFORMATION FOR SEQ ID NO: 155:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 155:

Cys Thr Arg Pro Asn Asn Asn Thr Arg Lys Ser Asn His Ile Gly Pro
1               5                   10                  15

Gly Arg Ala Trp Tyr Thr Thr Gly Asp Ile Ile Gly Asn Ile Arg Gln
            20                  25                  30

Ala His Cys
        35

(2) INFORMATION FOR SEQ ID NO: 156:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 156:

Cys Thr Arg Pro Asn Asn Asn Thr Arg Lys Ser Ile His Ile Gly Pro
1               5                   10                  15

Gly Arg Ala Trp Tyr Thr Thr Gly Asp Ile Ile Gly Asp Ile Arg Gln
            20                  25                  30

Ala His Cys
        35

(2) INFORMATION FOR SEQ ID NO: 157:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 157:

Cys Thr Arg Pro Asn Asn Asn Thr Arg Lys Ser Ile His Ile Gly Pro
1               5                   10                  15

Gly Arg Ala Trp Tyr Thr Thr Gly Asp Ile Ile Gly Asn Ile Arg Gln
            20                  25                  30

Ala His Cys
        35

(2) INFORMATION FOR SEQ ID NO: 158:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 158:

Cys Thr Arg Pro Asn Asn Asn Thr Arg Lys Ser Ile Pro Ile Gly Pro
1               5                   10                  15

Gly Arg Ala Trp Tyr Thr Thr Gly Asp Ile Ile Gly Asp Ile Arg Gln
            20                  25                  30

Ala His Cys
        35

(2) INFORMATION FOR SEQ ID NO: 159:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 159:

Cys Thr Arg Pro Asn Asn Asn Thr Arg Lys Ser Ile Pro Ile Gly Pro
1               5                   10                  15

Gly Arg Ala Trp Tyr Thr Thr Gly Asp Ile Ile Gly Asn Ile Arg Gln
            20                  25                  30

Ala His Cys
        35

(2) INFORMATION FOR SEQ ID NO: 160:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 160:

Cys Ile Arg Pro Asn Asn Asn Thr Arg Lys Ser Ile Thr Phe Gly Pro
1               5                   10                  15

Gly Gln Ala Phe Tyr Ala Thr Ser Asn Ile Ile Gly Asp Ile Arg Gln
            20                  25                  30

Ala His Cys
        35

(2) INFORMATION FOR SEQ ID NO: 161:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 161:

Cys Ile Arg Pro Asn Asn Asn Thr Arg Lys Ser Ile Thr Phe Gly Pro
1               5                   10                  15

Gly Gln Ala Phe Tyr Ala Thr Ser Asn Ile Ile Gly Asn Ile Arg Gln
            20                  25                  30

Ala Tyr Cys
        35

(2) INFORMATION FOR SEQ ID NO: 162:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 162:

Cys Ile Arg Pro Asn Asn Asn Thr Arg Lys Ser Ile Thr Phe Gly Pro
1               5                  10                  15

Gly Gln Ala Phe Tyr Ala Thr Ser Asn Ile Ile Gly Asp Ile Arg Gln
            20                  25                  30

Ala Tyr Cys
        35

(2) INFORMATION FOR SEQ ID NO: 163:

(i) SEQUENCE CHARACTERISTICS:
          (A) LENGTH: 35 amino acids
          (B) TYPE: amino acid
          (C) STRANDEDNESS: unknown
          (D) TOPOLOGY: circular (ii) MOLECULE TYPE: peptide (iii) HYPOTHETICAL: NO (xi) SEQUENCE DESCRIPTION: SEQ ID NO: 163:

Cys Thr Arg Pro Asn Asn Asn Thr Arg Lys Ser Ile His Ile Gly Pro
1               5                  10                  15

Gly Lys Ala Phe Tyr Ala Thr Gly Asp Ile Ile Gly Asp Ile Arg Gln
            20                  25                  30

Ala His Cys
        35

(2) INFORMATION FOR SEQ ID NO: 164:

(i) SEQUENCE CHARACTERISTICS:
          (A) LENGTH: 35 amino acids
          (B) TYPE: amino acid
          (C) STRANDEDNESS: unknown
          (D) TOPOLOGY: circular (ii) MOLECULE TYPE: peptide (iii) HYPOTHETICAL: NO (xi) SEQUENCE DESCRIPTION: SEQ ID NO: 164:

Cys Thr Arg Pro Asn Asn Asn Thr Arg Arg Gly Ile His Ile Gly Pro
1               5                  10                  15

Gly Arg Ala Phe Tyr Ala Thr Gly Asp Ile Ile Gly Asp Ile Arg Gln
            20                  25                  30

Ala His Cys
        35

(2) INFORMATION FOR SEQ ID NO: 165:

(i) SEQUENCE CHARACTERISTICS:
          (A) LENGTH: 35 amino acids
          (B) TYPE: amino acid
          (C) STRANDEDNESS: unknown
          (D) TOPOLOGY: circular (ii) MOLECULE TYPE: peptide (iii) HYPOTHETICAL: NO (xi) SEQUENCE DESCRIPTION: SEQ ID NO: 165:

Cys Thr Arg Pro Asn Asn Asn Thr Arg Lys Ser Ile His Ile Gly Pro
1               5                   10                  15

Gly Lys Ala Phe Tyr Thr Thr Gly Asp Ile Ile Gly Asp Ile Arg Gln
            20                  25                  30

Ala Tyr Cys
        35

(2) INFORMATION FOR SEQ ID NO: 166:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 166:

Cys Thr Arg Pro Asn Asn Asn Thr Arg Lys Ser Ile His Ile Gly Pro
1               5                   10                  15

Gly Lys Ala Phe Tyr Thr Thr Gly Asp Ile Ile Gly Asp Ile Arg Gln
            20                  25                  30

Ala His Cys
        35

(2) INFORMATION FOR SEQ ID NO: 167:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 167:

Cys Thr Arg Pro Asn Asn Asn Thr Arg Lys Ser Ile His Ile Gly Pro
1               5                   10                  15

Gly Arg Ala Phe Tyr Thr Thr Gly Glu Ile Val Gly Asp Ile Arg Gln
            20                  25                  30

Ala Tyr Cys
        35

(2) INFORMATION FOR SEQ ID NO: 168:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 168:

Cys Thr Arg Pro Asn Asn Asn Thr Arg Lys Ser Ile His Ile Gly Pro
1               5                   10                  15

Gly Arg Ala Phe Tyr Thr Thr Gly Asp Ile Val Gly Asp Ile Arg Gln
            20                  25                  30

Ala His Cys

35

(2) INFORMATION FOR SEQ ID NO: 169:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 169:

Cys Thr Arg Pro Asn Asn Asn Thr Arg Lys Ser Ile His Ile Gly Pro
1               5                   10                  15

Gly Arg Ala Phe Tyr Thr Thr Gly Glu Ile Ile Gly Asp Ile Arg Gln
            20                  25                  30

Ala Tyr Cys
        35

(2) INFORMATION FOR SEQ ID NO: 170:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 170:

Cys Thr Arg Pro Asn Asn Asn Thr Arg Lys Ser Ile His Ile Gly Pro
1               5                   10                  15

Gly Arg Ala Phe Tyr Thr Thr Gly Glu Ile Val Gly Asp Ile Arg Gln
            20                  25                  30

Ala His Cys
        35

(2) INFORMATION FOR SEQ ID NO: 171:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 171:

Cys Thr Arg Pro Ser Asn Asn Thr Arg Lys Gly Ile His Ile Gly Pro
1               5                   10                  15

Gly Arg Ala Phe Tyr Thr Thr Gly Glu Ile Thr Gly Asp Ile Arg Gln
            20                  25                  30

Ala His Cys
        35

(2) INFORMATION FOR SEQ ID NO: 172:

(i) SEQUENCE CHARACTERISTICS:
        (A) LENGTH: 35 amino acids (B) TYPE: amino acid
            (C) STRANDEDNESS: unknown
            (D) TOPOLOGY: circular (ii) MOLECULE TYPE: peptide (iii) HYPOTHETICAL: NO (xi) SEQUENCE DESCRIPTION: SEQ ID NO: 172:

Cys Ser Arg Pro Asn Asn Asn Thr Arg Arg Ser Val His Ile Gly Pro
1               5                   10                  15

Gly Arg Ala Trp Tyr Thr Thr Gly Asp Ile Ile Gly Asn Ile Arg Gln
            20                  25                  30

Ala His Cys
        35

(2) INFORMATION FOR SEQ ID NO: 173:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 173:

Cys Ser Arg Pro Asn Asn Asn Thr Arg Lys Val Ile Pro Ile Gly Pro
1               5                   10                  15

Gly Arg Ala Trp Tyr Thr Thr Gly Asp Ile Ile Gly Asp Ile Arg Gln
            20                  25                  30

Ala His Cys
        35

(2) INFORMATION FOR SEQ ID NO: 174:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 174:

Cys Ile Arg Pro Asn Asn Asn Thr Lys Lys Ser Ile Thr Phe Gly Pro
1               5                   10                  15

Gly Gln Ala Phe Tyr Ala Thr Ser Asn Ile Ile Gly Asn Ile Arg Gln
            20                  25                  30

Ala Tyr Cys
        35

(2) INFORMATION FOR SEQ ID NO: 175:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 175:

Cys Ile Arg Pro Asn Asn Asn Thr Arg Lys Ser Ile Thr Phe Gly Pro
1               5                   10                  15

Gly Gln Ala Phe Tyr Ala Thr Ser Asn Ile Ile Gly Asp Ile Lys Gln
            20                  25                  30

Ala Tyr Cys
        35

(2) INFORMATION FOR SEQ ID NO: 176:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 176:

Cys Thr Arg Pro Asn Asn Asn Thr Arg Arg Gly Ile Asn Ile Gly Pro
1               5                   10                  15

Gly Arg Ala Phe Tyr Thr Thr Gly Asp Ile Ile Gly Asp Ile Arg Gln
            20                  25                  30

Ala His Cys
        35

(2) INFORMATION FOR SEQ ID NO: 177:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 177:

Cys Thr Arg Pro Asn Asn Asn Thr Arg Arg Gly Ile His Ile Gly Pro
1               5                   10                  15

Gly Arg Ala Phe Tyr Thr Thr Gly Asp Ile Ile Gly Asp Ile Arg Gln
            20                  25                  30

Ala His Cys
        35

(2) INFORMATION FOR SEQ ID NO: 178:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 178:

Cys Thr Arg Pro Asn Asn Asn Thr Arg Lys Ser Ile Gln Met Gly Pro
1               5                   10                  15

Gly Arg Ala Phe Tyr Thr Thr Gly Glu Ile Ile Gly Asp Ile Arg Gln

```
            20                  25                  30

Ala His Cys
        35

(2) INFORMATION FOR SEQ ID NO: 179:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 179:

Cys Thr Arg Pro Asn Asn Asn Thr Arg Lys Gly Ile His Met Gly Pro
1               5                   10                  15

Gly Lys Ala Phe Tyr Thr Thr Gly Glu Ile Ile Gly Asp Ile Arg Gln
            20                  25                  30

Ala His Cys
        35

(2) INFORMATION FOR SEQ ID NO: 180:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 180:

Cys Thr Arg Pro Asn Asn Asn Thr Arg Lys Ser Ile Gln Met Gly Pro
1               5                   10                  15

Gly Lys Ala Phe Tyr Thr Thr Gly Glu Ile Ile Gly Asp Ile Arg Gln
            20                  25                  30

Ala His Cys
        35

(2) INFORMATION FOR SEQ ID NO: 181:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 181:

Cys Thr Arg Pro Asn Asn Asn Thr Arg Lys Ser Ile Asn Met Gly Pro
1               5                   10                  15

Gly Arg Ala Phe Tyr Thr Thr Gly Glu Ile Ile Gly Asp Ile Arg Gln
            20                  25                  30

Ala His Cys
        35

(2) INFORMATION FOR SEQ ID NO: 182:
```

(i) SEQUENCE CHARACTERISTICS:
    (A) LENGTH: 35 amino acids
    (B) TYPE: amino acid
    (C) STRANDEDNESS: unknown
    (D) TOPOLOGY: circular (ii) MOLECULE TYPE: peptide (iii) HYPOTHETICAL: NO (xi) SEQUENCE DESCRIPTION: SEQ ID NO: 182:

Cys Thr Arg Pro Asn Asn Asn Thr Arg Lys Ser Ile His Met Gly Pro
1               5                   10                  15

Gly Lys Ala Phe Tyr Thr Thr Gly Glu Ile Ile Gly Asp Ile Arg Gln
            20                  25                  30

Ala His Cys
        35

(2) INFORMATION FOR SEQ ID NO: 183:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 183:

Cys Thr Arg Pro Asn Asn Asn Thr Arg Lys Gly Ile Gln Met Gly Pro
1               5                   10                  15

Gly Lys Ala Phe Tyr Thr Thr Gly Glu Ile Ile Gly Asp Ile Arg Gln
            20                  25                  30

Ala His Cys
        35

(2) INFORMATION FOR SEQ ID NO: 184:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 184:

Cys Thr Arg Pro Asn Asn Asn Thr Arg Lys Ser Ile Gln Met Gly Pro
1               5                   10                  15

Gly Lys Ala Phe Tyr Thr Thr Gly Glu Ile Ile Gly Glu Ile Arg Gln
            20                  25                  30

Ala His Cys
        35

(2) INFORMATION FOR SEQ ID NO: 185:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 185:

Cys Thr Arg Pro Asn Asn Asn Thr Arg Lys Ser Ile His Met Gly Pro
1               5                   10                  15

Gly Arg Ala Phe Tyr Thr Thr Gly Glu Ile Ile Gly Asp Ile Arg Gln
            20                  25                  30

Ala His Cys
        35

(2) INFORMATION FOR SEQ ID NO: 186:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 186:

Cys Thr Arg Pro Asn Asn Asn Thr Arg Lys Ser Ile His Ile Gly Pro
1               5                   10                  15

Gly Arg Ala Val Tyr Thr Thr Gly Glu Ile Ile Gly Asp Ile Arg Gln
            20                  25                  30

Ala His Cys
        35

(2) INFORMATION FOR SEQ ID NO: 187:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 187:

Cys Thr Arg Pro Asn Asn Asn Thr Arg Lys Ser Ile His Ile Gly Pro
1               5                   10                  15

Gly Arg Ala Phe Tyr Ser Thr Gly Gln Ile Ile Gly Asp Ile Arg Gln
            20                  25                  30

Ala His Cys
        35

(2) INFORMATION FOR SEQ ID NO: 188:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 188:

Cys Thr Arg Pro Asn Asn Asn Thr Arg Lys Ser Ile His Ile Gly Pro

```
             1               5              10              15

Gly Arg Ala Phe Tyr Thr Thr Gly Gln Ile Ile Gly Asp Ile Arg Gln
                20                  25                  30

Ala His Cys
        35
```

(2) INFORMATION FOR SEQ ID NO: 189:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 189:

```
Cys Thr Arg Pro Asn Asn Asn Thr Arg Lys Ser Ile His Ile Ala Pro
  1               5                  10                  15

Gly Ser Ala Phe Tyr Ala Thr Gly Ala Ile Ile Gly Asp Ile Arg Lys
                20                  25                  30

Ala His Cys
        35
```

(2) INFORMATION FOR SEQ ID NO: 190:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 190:

```
Cys Thr Arg Pro Asn Asn Asn Thr Arg Arg Ser Ile His Ile Ala Pro
  1               5                  10                  15

Gly Arg Ala Phe Tyr Ala Thr Gly Ala Ile Ile Gly Asp Ile Arg Lys
                20                  25                  30

Ala His Cys
        35
```

(2) INFORMATION FOR SEQ ID NO: 191:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 191:

```
Cys Thr Arg Pro Asn Asn Asn Thr Arg Lys Arg Val Thr Met Gly Pro
  1               5                  10                  15

Gly Arg Val Trp Tyr Thr Thr Gly Glu Ile Ile Gly Asn Ile Lys Gln
                20                  25                  30

Ala His Cys
        35
```

(2) INFORMATION FOR SEQ ID NO: 192:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 192:

```
Cys Thr Arg Pro Asn Asn Asn Thr Arg Lys Arg Val Thr Met Gly Pro
1               5                   10                  15

Gly Arg Val Leu Tyr Thr Thr Gly Glu Ile Ile Gly Asp Ile Lys Gln
            20                  25                  30

Ala His Cys
        35
```

(2) INFORMATION FOR SEQ ID NO: 193:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 193:

```
Cys Thr Arg Pro Asn Asn Asn Thr Arg Lys Gly Ile His Leu Gly Pro
1               5                   10                  15

Gly Gly Thr Phe Tyr Ala Thr Gly Asp Ile Ile Gly Asp Ile Arg Gln
            20                  25                  30

Ala His Cys
        35
```

(2) INFORMATION FOR SEQ ID NO: 194:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 194:

```
Cys Thr Arg Pro Asn Asn Asn Thr Arg Lys Gly Ile His Ile Gly Pro
1               5                   10                  15

Gly Arg Ala Ile Tyr Thr Thr Ser Lys Ile Ile Gly Asp Ile Arg Gln
            20                  25                  30

Ala His Cys
        35
```

(2) INFORMATION FOR SEQ ID NO: 195:

(i) SEQUENCE CHARACTERISTICS:
        (A) LENGTH: 35 amino acids
        (B) TYPE: amino acid

```
            (C) STRANDEDNESS: unknown
            (D) TOPOLOGY: circular (ii) MOLECULE TYPE: peptide (iii) HYPOTHETICAL: NO (xi) SEQUENCE DESCRIPTION: SEQ ID NO: 195:

Cys Thr Arg Pro Asn Asn Asn Thr Arg Lys Ser Ile His Met Gly Pro
1               5                  10                  15

Gly Arg Ala Phe Tyr Thr Thr Gly Lys Ile Ile Gly Asp Ile Arg Gln
            20                  25                  30

Ala His Cys
        35

(2) INFORMATION FOR SEQ ID NO: 196:

(i) SEQUENCE CHARACTERISTICS:
            (A) LENGTH: 35 amino acids
            (B) TYPE: amino acid
            (C) STRANDEDNESS: unknown
            (D) TOPOLOGY: circular (ii) MOLECULE TYPE: peptide (iii) HYPOTHETICAL: NO (xi) SEQUENCE DESCRIPTION: SEQ ID NO: 196:

Cys Thr Arg Pro Asn Asn Asn Thr Arg Lys Ser Ile Pro Ile Gly Pro
1               5                  10                  15

Gly Arg Ala Ile Tyr Thr Thr Gly Asp Ile Ile Gly Asn Ile Arg Gln
            20                  25                  30

Ala His Cys
        35

(2) INFORMATION FOR SEQ ID NO: 197:

(i) SEQUENCE CHARACTERISTICS:
            (A) LENGTH: 34 amino acids
            (B) TYPE: amino acid
            (C) STRANDEDNESS: unknown
            (D) TOPOLOGY: circular (ii) MOLECULE TYPE: peptide (iii) HYPOTHETICAL: NO (xi) SEQUENCE DESCRIPTION: SEQ ID NO: 197:

Cys Thr Arg Pro Asn Asn Asn Lys Arg Gln Ser Ile His Ile Gly Pro
1               5                  10                  15

Gly Arg Ala Phe Phe Gly Thr Asp Ile Ile Gly Asn Ile Arg Gln Ala
            20                  25                  30

Tyr Cys (2) INFORMATION FOR SEQ ID NO: 198:

(i) SEQUENCE CHARACTERISTICS:
            (A) LENGTH: 34 amino acids
            (B) TYPE: amino acid
            (C) STRANDEDNESS: unknown
            (D) TOPOLOGY: circular (ii) MOLECULE TYPE: peptide (iii) HYPOTHETICAL: NO (xi) SEQUENCE DESCRIPTION: SEQ ID NO: 198:
```

Cys Thr Arg Pro Asn Arg Asn Lys Ile Arg Arg Ile His Ile Gly Pro
1               5                   10                  15

Gly Arg Pro Phe Tyr Gly Thr Asp Ile Glu Gly Pro Ile Arg Gln Ala
            20                  25                  30

Tyr Cys (2) INFORMATION FOR SEQ ID NO: 199:

(i) SEQUENCE CHARACTERISTICS:
        (A) LENGTH: 34 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 199:

Cys Thr Arg Pro Thr Arg Asn Lys Ile Arg Arg Ile His Ile Gly Pro
1               5                   10                  15

Gly Arg Pro Phe Tyr Gly Thr Asp Ile Thr Gly Pro Ile Arg Gln Ala
            20                  25                  30

Tyr Cys (2) INFORMATION FOR SEQ ID NO: 200:

(i) SEQUENCE CHARACTERISTICS:
        (A) LENGTH: 34 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 200:

Cys Thr Arg Pro Asn Arg Asn Lys Ile Arg Arg Ile His Ile Gly Pro
1               5                   10                  15

Gly Arg Pro Phe Tyr Gly Thr Asp Ile Glu Gly Thr Ile Arg Gln Ala
            20                  25                  30

Tyr Cys (2) INFORMATION FOR SEQ ID NO: 201:

(i) SEQUENCE CHARACTERISTICS:
        (A) LENGTH: 34 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 201:

Cys Thr Arg Pro Asn Asn Thr Arg Lys Ser Ile His Ile Gly Pro
1               5                   10                  15

Gly Arg Ala Phe Tyr Gly Thr Asp Ile Val Gly Asn Ile Arg Gln Ala
            20                  25                  30

Tyr Cys (2) INFORMATION FOR SEQ ID NO: 202:

(i) SEQUENCE CHARACTERISTICS:
        (A) LENGTH: 38 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 202:

```
Cys Thr Arg Leu Gly Asn Lys Thr Arg Arg Gly Val His Ile Lys His
 1               5                  10                  15

Ile Gly Pro Gly Arg Val Phe Tyr Thr Thr Gly Ala Val Ile Gly Asp
             20                  25                  30

Ile Arg Arg Ala His Cys
         35
```

(2) INFORMATION FOR SEQ ID NO: 203:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 203:

```
Cys Thr Arg Leu Ser Asn Asn Thr Arg Arg Gly Val His Ile Gly Pro
 1               5                  10                  15

Gly Arg Ala Phe Tyr Thr Thr Gly Thr Val Ile Gly Asp Ile Arg Gln
             20                  25                  30

Ala His Cys
         35
```

(2) INFORMATION FOR SEQ ID NO: 204:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 204:

```
Cys Thr Arg Leu Ser Asn Asn Thr Arg Arg Gly Val His Ile Gly Pro
 1               5                  10                  15

Gly Arg Ala Phe Tyr Thr Thr Gly Ala Val Ile Gly Asp Ile Arg Gln
             20                  25                  30

Gly His Cys
         35
```

(2) INFORMATION FOR SEQ ID NO: 205:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 205:

Cys Thr Arg Leu Ser Asn Asn Thr Arg Arg Gly Val His Ile Gly Pro
1               5                  10                 15

Gly Arg Ala Phe Tyr Thr Thr Gly Ala Val Ile Gly Asp Ile Arg Gln
            20                  25                  30

Ala His Cys
        35

(2) INFORMATION FOR SEQ ID NO: 206:

(i) SEQUENCE CHARACTERISTICS:
         (A) LENGTH: 38 amino acids
         (B) TYPE: amino acid
         (C) STRANDEDNESS: unknown
         (D) TOPOLOGY: circular (ii) MOLECULE TYPE: peptide (iii) HYPOTHETICAL: NO (xi) SEQUENCE DESCRIPTION: SEQ ID NO: 206:

Cys Thr Arg Leu Ser Asn Asn Thr Arg Arg Gly Val His Ile Lys His
1               5                  10                 15

Ile Gly Pro Gly Arg Val Phe Tyr Thr Thr Gly Ala Val Ile Gly Asp
            20                  25                  30

Ile Arg Arg Ala His Cys
        35

(2) INFORMATION FOR SEQ ID NO: 207:

(i) SEQUENCE CHARACTERISTICS:
         (A) LENGTH: 35 amino acids
         (B) TYPE: amino acid
         (C) STRANDEDNESS: unknown
         (D) TOPOLOGY: circular (ii) MOLECULE TYPE: peptide (iii) HYPOTHETICAL: NO (xi) SEQUENCE DESCRIPTION: SEQ ID NO: 207:

Cys Thr Arg Pro Asn Asn Asn Thr Arg Lys Ser Ile Asn Ile Gly Pro
1               5                  10                 15

Gly Arg Ala Phe Tyr Ala Thr Gly Asp Ile Ile Gly Asp Ile Arg Gln
            20                  25                  30

Ala His Cys
        35

(2) INFORMATION FOR SEQ ID NO: 208:

(i) SEQUENCE CHARACTERISTICS:
         (A) LENGTH: 38 amino acids
         (B) TYPE: amino acid
         (C) STRANDEDNESS: unknown
         (D) TOPOLOGY: circular (ii) MOLECULE TYPE: peptide (iii) HYPOTHETICAL: NO (xi) SEQUENCE DESCRIPTION: SEQ ID NO: 208:

```
Cys Thr Arg Pro Asn Asn Asn Thr Arg Lys Gly Ile Arg Ile Gly His
1               5                   10                  15

Ile Gly Pro Gly Arg Val Phe Tyr Thr Thr Gly Lys Ile Ile Gly Asp
            20                  25                  30

Ile Arg Gln Ala His Cys
            35
```

(2) INFORMATION FOR SEQ ID NO: 209:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 209:

```
Cys Thr Arg Pro Asn Asn Asn Thr Arg Lys Gly Ile His Ile Gly Pro
1               5                   10                  15

Gly Arg Ala Val Tyr Thr Thr Gly Arg Ile Ile Gly Asp Ile Arg Gln
            20                  25                  30

Ala His Cys
        35
```

(2) INFORMATION FOR SEQ ID NO: 210:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 210:

```
Cys Thr Arg Pro Asn Asn Asn Thr Arg Arg Gly Ile Tyr Ile Gly Pro
1               5                   10                  15

Gly Arg Ala Val Tyr Thr Lys Gly Arg Ile Ile Gly Asp Ile Arg Gln
            20                  25                  30

Ala His Cys
        35
```

(2) INFORMATION FOR SEQ ID NO: 211:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 211:

```
Cys Thr Arg Pro Asn Asn Asn Arg Lys Ser Ile Asn Ile Gly Pro
1               5                   10                  15

Gly Arg Ala Phe Tyr Ala Thr Gly Glu Ile Ile Gly Asp Ile Arg Gln
            20                  25                  30

Ala His Cys
```

35

(2) INFORMATION FOR SEQ ID NO: 212:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 212:

Cys Thr Arg Pro Ser Asn Asn Thr Arg Lys Ser Ile His Ile Gly Pro
1               5                   10                  15

Gly Arg Ala Phe Tyr Thr Thr Gly Asp Ile Ile Gly Asp Ile Arg Gln
            20                  25                  30

Ala His Cys
        35

(2) INFORMATION FOR SEQ ID NO: 213:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 213:

Cys Thr Arg Pro Asn Asn Asn Thr Arg Lys Gly Ile His Ile Gly Pro
1               5                   10                  15

Gly Arg Thr Phe Tyr Thr Thr Gly Glu Ile Ile Gly Asp Ile Arg Gln
            20                  25                  30

Ala His Cys
        35

(2) INFORMATION FOR SEQ ID NO: 214:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 214:

Cys Thr Arg Pro Asn Asn Asn Thr Arg Lys Ser Ile His Ile Gly Pro
1               5                   10                  15

Gly Ser Ala Val Tyr Thr Thr Gly Glu Ile Ile Gly Asp Ile Arg Gln
            20                  25                  30

Ala His Cys
        35

(2) INFORMATION FOR SEQ ID NO: 215:

(i) SEQUENCE CHARACTERISTICS:
        (A) LENGTH: 35 amino acids (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 215:

Cys Thr Arg Pro Asn Asn Asn Thr Arg Lys Ser Ile Pro Met Gly Pro
1               5                   10                  15

Gly Lys Ala Phe Tyr Ala Thr Gly Asp Ile Ile Gly Asp Ile Arg Lys
            20                  25                  30

Ala Tyr Cys
        35

(2) INFORMATION FOR SEQ ID NO: 216:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 216:

Cys Thr Arg Pro Asn Asn Asn Thr Arg Lys Ser Ile Gly Leu Gly Pro
1               5                   10                  15

Gly Arg Ala Phe Tyr Ala Thr Gly Asp Ile Ile Gly Asp Ile Arg Gln
            20                  25                  30

Ala His Cys
        35

(2) INFORMATION FOR SEQ ID NO: 217:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 217:

Cys Thr Arg Pro Asn Asn Asn Thr Arg Lys Gly Ile His Ile Gly Pro
1               5                   10                  15

Gly Lys Ala Phe Tyr Ala Thr Gly Asp Ile Ile Gly Asp Ile Arg Gln
            20                  25                  30

Ala His Cys
        35

(2) INFORMATION FOR SEQ ID NO: 218:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 218:

Cys Thr Arg Pro Asn Asn Tyr Thr Arg Lys Gly Ile Arg Ile Gly Pro
1               5                   10                  15

Gly Ser Ala Val Tyr Ala Ala Glu Lys Ile Ile Gly Asp Ile Arg Gln
            20                  25                  30

Ala His Cys
        35

(2) INFORMATION FOR SEQ ID NO: 219:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 219:

Cys Thr Arg Pro Asn Asn Asn Thr Arg Lys Gly Ile His Ile Gly Pro
1               5                   10                  15

Gly Ser Ala Phe Tyr Ala Thr Gly Asp Ile Ile Gly Asp Ile Arg Gln
            20                  25                  30

Ala His Cys
        35

(2) INFORMATION FOR SEQ ID NO: 220:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 220:

Cys Thr Arg Pro Asn Asn Tyr Thr Arg Lys Gly Ile Arg Ile Gly Pro
1               5                   10                  15

Gly Ser Ala Val Ile Ala Thr Glu Lys Ile Ile Gly Asp Ile Arg Gln
            20                  25                  30

Ala His Cys
        35

(2) INFORMATION FOR SEQ ID NO: 221:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 221:

Cys Thr Arg Pro Asn Asn Asn Thr Arg Lys Gly Ile His Ile Gly Pro
1               5                   10                  15

Gly Arg Ala Phe Phe Ala Thr Gly Asp Ile Ile Gly Asp Ile Arg Gln

```
                    20                  25                  30
Ala His Cys
        35

(2) INFORMATION FOR SEQ ID NO: 222:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 222:

Cys Thr Arg Pro Asn Asn Tyr Thr Arg Lys Gly Ile Arg Ile Gly Pro
1               5                  10                  15

Gly Arg Ala Val Ile Ala Thr Glu Lys Ile Ile Gly Asp Ile Arg Gln
            20                  25                  30

Ala His Cys
        35

(2) INFORMATION FOR SEQ ID NO: 223:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 223:

Cys Thr Arg Pro Asn Asn Asn Thr Arg Lys Gly Ile Arg Ile Gly Pro
1               5                  10                  15

Gly Arg Ala Val Tyr Ala Thr Glu Lys Ile Ile Gly Asp Ile Arg Gln
            20                  25                  30

Ala His Cys
        35

(2) INFORMATION FOR SEQ ID NO: 224:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 224:

Cys Thr Arg Pro Asn Asn Asn Thr Arg Lys Gly Ile His Ile Gly Pro
1               5                  10                  15

Gly Arg Ala Phe Tyr Ala Ala Gly Arg Val Ile Gly Asp Ile Arg Gln
            20                  25                  30

Ala His Cys
        35

(2) INFORMATION FOR SEQ ID NO: 225:
```

(i) SEQUENCE CHARACTERISTICS:
            (A) LENGTH: 35 amino acids
            (B) TYPE: amino acid
            (C) STRANDEDNESS: unknown
            (D) TOPOLOGY: circular (ii) MOLECULE TYPE: peptide (iii) HYPOTHETICAL: NO (xi) SEQUENCE DESCRIPTION: SEQ ID NO: 225:

Cys Thr Arg Pro Asn Asn Asn Thr Arg Arg Ser Ile Pro Ile Gly Pro
1               5                  10                  15

Gly Arg Ala Phe Tyr Ala Thr Gly Gln Ile Ile Gly Asp Ile Arg Gln
            20                  25                  30

Ala His Cys
        35

(2) INFORMATION FOR SEQ ID NO: 226:

(i) SEQUENCE CHARACTERISTICS:
            (A) LENGTH: 35 amino acids
            (B) TYPE: amino acid
            (C) STRANDEDNESS: unknown
            (D) TOPOLOGY: circular (ii) MOLECULE TYPE: peptide (iii) HYPOTHETICAL: NO (xi) SEQUENCE DESCRIPTION: SEQ ID NO: 226:

Cys Thr Arg Pro Asn Asn Asn Thr Lys Arg Ser Ile Ser Ile Gly Pro
1               5                  10                  15

Gly Arg Ala Phe Tyr Ala Thr Gly Lys Ile Ile Gly Asp Ile Arg Gln
            20                  25                  30

Ala His Cys
        35

(2) INFORMATION FOR SEQ ID NO: 227:

(i) SEQUENCE CHARACTERISTICS:
            (A) LENGTH: 35 amino acids
            (B) TYPE: amino acid
            (C) STRANDEDNESS: unknown
            (D) TOPOLOGY: circular (ii) MOLECULE TYPE: peptide (iii) HYPOTHETICAL: NO (xi) SEQUENCE DESCRIPTION: SEQ ID NO: 227:

Cys Thr Arg Pro Asn Asn Asn Ile Lys Arg Ser Ile Ser Ile Gly Pro
1               5                  10                  15

Gly Arg Ala Phe Tyr Ala Thr Gly Lys Ile Ile Gly Asp Ile Arg Gln
            20                  25                  30

Ala His Cys
        35

(2) INFORMATION FOR SEQ ID NO: 228:

(i) SEQUENCE CHARACTERISTICS:
            (A) LENGTH: 35 amino acids
            (B) TYPE: amino acid
            (C) STRANDEDNESS: unknown
            (D) TOPOLOGY: circular (ii) MOLECULE TYPE: peptide (iii) HYPOTHETICAL: NO (xi) SEQUENCE DESCRIPTION: SEQ ID NO: 228:

Cys Thr Arg Pro Asn Asn Asn Thr Arg Arg Ser Ile Pro Ile Gly Pro
1               5                   10                  15

Gly Gly Ala Phe Tyr Ala Thr Glu Arg Ile Ile Gly Asp Ile Arg Gln
            20                  25                  30

Ala His Cys
        35

(2) INFORMATION FOR SEQ ID NO: 229:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 229:

Cys Thr Arg Pro Asn Asn Asn Ile Lys Arg Ser Ile Ser Ile Gly Pro
1               5                   10                  15

Gly Arg Ala Phe Tyr Ala Thr Gly Gln Ile Ile Gly Asp Ile Arg Gln
            20                  25                  30

Ala His Cys
        35

(2) INFORMATION FOR SEQ ID NO: 230:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 230:

Cys Thr Arg Pro Asn Asn Asn Ile Lys Arg Ser Ile Ser Met Gly Pro
1               5                   10                  15

Gly Arg Ala Phe Tyr Ala Thr Gly Gln Ile Ile Gly Asp Ile Arg Gln
            20                  25                  30

Ala His Cys
        35

(2) INFORMATION FOR SEQ ID NO: 231:

(i) SEQUENCE CHARACTERISTICS:
        (A) LENGTH: 35 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO: 231:

Cys Thr Arg Pro Asn Asn Asn Ile Lys Arg Ser Ile Ser Ile Gly Pro

```
             1               5              10              15
Gly Arg Ala Phe Tyr Ala Thr Gly Gln Ile Ile Gly Asp Ile Arg Gln
                    20                  25                  30

Val His Cys
        35

(2) INFORMATION FOR SEQ ID NO: 232:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 232:

Cys Thr Arg Pro Asn Asn Asn Ile Lys Arg Ser Ile Ser Met Gly Pro
1               5                  10                  15

Gly Arg Ala Phe Tyr Ala Thr Gly Gln Ile Ile Gly Asp Ile Arg Glu
                    20                  25                  30

Ala His Cys
        35

(2) INFORMATION FOR SEQ ID NO: 233:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 233:

Cys Thr Arg Pro Asn Asn Asn Lys Arg Arg Ser Ile Pro Ile Gly Pro
1               5                  10                  15

Gly Gly Ala Phe Tyr Ala Thr Glu Arg Ile Ile Gly Asp Ile Arg Glu
                    20                  25                  30

Ala His Cys
        35

(2) INFORMATION FOR SEQ ID NO: 234:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 234:

Cys Thr Arg Pro Asn Asn Asn Thr Arg Lys Ser Ile His Ile Gly Pro
1               5                  10                  15

Gly Gln Ala Phe Tyr Ala Asn Ser Pro Ile Ile Gly Asn Ile Arg Gln
                    20                  25                  30

Ala Tyr Cys
        35
```

(2) INFORMATION FOR SEQ ID NO: 235:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 235:

```
Cys Thr Arg Pro Asn Asn Asn Thr Arg Lys Ser Ile His Ile Gly Pro
 1               5                  10                  15

Gly Gln Ala Phe Tyr Ala Asn Ser Arg Ile Ile Gly Asp Ile Arg Asn
                20                  25                  30

Ala His Cys
        35
```

(2) INFORMATION FOR SEQ ID NO: 236:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 236:

```
Cys Ile Arg Pro Asn Asn Asn Thr Arg Gln Ser Ile His Ile Gly Pro
 1               5                  10                  15

Gly Gln Ala Phe Tyr Ala Asn Ser Pro Ile Ile Gly Asp Ile Arg Gln
                20                  25                  30

Ala His Cys
        35
```

(2) INFORMATION FOR SEQ ID NO: 237:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 237:

```
Cys Ile Arg Pro Asn Asn Asn Thr Arg Gln Ser Ile His Ile Gly Pro
 1               5                  10                  15

Gly Gln Ala Phe Tyr Ala His Ser Pro Ile Ile Gly Asp Ile Arg Gln
                20                  25                  30

Ala His Cys
        35
```

(2) INFORMATION FOR SEQ ID NO: 238:

(i) SEQUENCE CHARACTERISTICS:
        (A) LENGTH: 35 amino acids
        (B) TYPE: amino acid (C) STRANDEDNESS: unknown
            (D) TOPOLOGY: circular (ii) MOLECULE TYPE: peptide (iii) HYPOTHETICAL: NO (xi) SEQUENCE DESCRIPTION: SEQ ID NO: 238:

Cys Thr Arg Pro Asn Asn Asn Thr Arg Lys Ser Ile Pro Met Gly Pro
1               5                   10                  15

Gly Arg Ala Phe Tyr Thr Thr Gly Asp Ile Ile Gly Asp Ile Arg Gln
            20                  25                  30

Ala His Cys
        35

(2) INFORMATION FOR SEQ ID NO: 239:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 239:

Cys Thr Arg Pro Asn Ser Asn Thr Arg Lys Ser Ile Arg Ile His Arg
1               5                   10                  15

Gly Arg Ala Phe Tyr Thr Thr Gly Asn Ile Ile Gly Asp Ile Arg Gln
            20                  25                  30

Ala His Cys
        35

(2) INFORMATION FOR SEQ ID NO: 240:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 240:

Cys Thr Arg Pro Asn Asn Asn Thr Arg Lys Arg Val Thr Leu Gly Pro
1               5                   10                  15

Gly Arg Val Trp Tyr Thr Thr Gly Glu Ile Ile Gly Asp Ile Arg Lys
            20                  25                  30

Ala Tyr Cys
        35

(2) INFORMATION FOR SEQ ID NO: 241:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO

```
    (xi) SEQUENCE DESCRIPTION: SEQ ID NO: 241:

Cys Thr Arg Pro Asn Asn Val Arg Lys Arg Ile Ser Leu Ser Pro
1               5                   10                  15

Gly Arg Val Phe Tyr Thr Thr Gly Glu Ile Ile Gly Asp Ile Arg Lys
            20                  25                  30

Ala His Cys
        35

(2) INFORMATION FOR SEQ ID NO: 242:

(i) SEQUENCE CHARACTERISTICS:
         (A) LENGTH: 35 amino acids
         (B) TYPE: amino acid
         (C) STRANDEDNESS: unknown
         (D) TOPOLOGY: circular (ii) MOLECULE TYPE: peptide (iii) HYPOTHETICAL: NO (xi) SEQUENCE DESCRIPTION: SEQ ID NO: 242:

Cys Thr Arg Pro Asn Asn Asn Ile Lys Arg Arg Ile Ile His Ile Gly
1               5                   10                  15

Pro Gly Arg Ala His Ala Thr Thr Gly Gly Ile Gly Asp Ile Arg Gln
            20                  25                  30

Ala His Cys
        35

(2) INFORMATION FOR SEQ ID NO: 243:

(i) SEQUENCE CHARACTERISTICS:
         (A) LENGTH: 35 amino acids
         (B) TYPE: amino acid
         (C) STRANDEDNESS: unknown
         (D) TOPOLOGY: circular (ii) MOLECULE TYPE: peptide (iii) HYPOTHETICAL: NO (xi) SEQUENCE DESCRIPTION: SEQ ID NO: 243:

Cys Thr Arg Pro Asn Asn Asn Thr Arg Lys Ser Ile His Leu Gly Pro
1               5                   10                  15

Gly Lys Ala Phe Tyr Thr Thr Gly Asp Ile Ile Gly Asp Ile Arg Gln
            20                  25                  30

Ala His Cys
        35

(2) INFORMATION FOR SEQ ID NO: 244:

(i) SEQUENCE CHARACTERISTICS:
         (A) LENGTH: 35 amino acids
         (B) TYPE: amino acid
         (C) STRANDEDNESS: unknown
         (D) TOPOLOGY: circular (ii) MOLECULE TYPE: peptide (iii) HYPOTHETICAL: NO (xi) SEQUENCE DESCRIPTION: SEQ ID NO: 244:

Cys Thr Arg Pro Asn Asn Asn Thr Lys Lys Gly Ile Ala Val Gly Pro
1               5                   10                  15

Gly Arg Asp Ile Tyr Thr Ala Asp Lys Ile Ile Gly Asp Leu Lys Gln
            20                  25                  30
```

Ala His Cys
    35

(2) INFORMATION FOR SEQ ID NO: 245:

(i) SEQUENCE CHARACTERISTICS:
        (A) LENGTH: 34 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 245:

Cys Thr Arg Pro Asn Asn Asn Thr Arg Arg Ser Ile His Ile Gly Pro
1               5                   10                  15

Gly Arg Ala Phe Phe Gly Thr Asp Ile Ile Gly Asn Ile Arg Gln Ala
            20                  25                  30

His Cys (2) INFORMATION FOR SEQ ID NO: 246:

(i) SEQUENCE CHARACTERISTICS:
        (A) LENGTH: 34 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 246:

Cys Thr Arg Pro Asn Asn Asn Thr Arg Arg Gly Ile His Ile Gly Pro
1               5                   10                  15

Gly Arg Ala Phe Tyr Gly Thr Asp Ile Ile Gly Asn Ile Arg Gln Ala
            20                  25                  30

His Cys (2) INFORMATION FOR SEQ ID NO: 247:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 247:

Cys Thr Arg Pro His Asn Asn Thr Arg Arg Gly Ile His Ile Gly Pro
1               5                   10                  15

Gly Arg Ala Phe Tyr Thr Thr Gly Ser Ile Thr Gly Asp Ile Arg Gln
            20                  25                  30

Ala His Cys
        35

(2) INFORMATION FOR SEQ ID NO: 248:

(i) SEQUENCE CHARACTERISTICS:
        (A) LENGTH: 35 amino acids (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 248:

Cys Thr Arg Pro Gly Asn Asn Thr Arg Lys Ser Val Arg Ile Gly Pro
1               5                  10                  15

Gly Gln Thr Phe Tyr Ala Thr Gly Ala Ile Ile Gly Asn Ile Arg Gln
            20                  25                  30

Ala His Cys
        35

(2) INFORMATION FOR SEQ ID NO: 249:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 249:

Cys Thr Arg Pro Gly Asn Asn Thr Arg Lys Ser Val Arg Ile Gly Pro
1               5                  10                  15

Gly Gln Thr Phe Tyr Ala Thr Gly Ala Ile Thr Gly Asn Ile Arg Gln
            20                  25                  30

Ala His Cys
        35

(2) INFORMATION FOR SEQ ID NO: 250:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 250:

Cys Thr Arg Pro Asn Asn Asn Thr Arg Lys Ser Val Arg Ile Gly Pro
1               5                  10                  15

Gly Gln Thr Phe Tyr Ala Thr Gly Asp Ile Ile Gly Asn Ile Arg Gln
            20                  25                  30

Ala His Cys
        35

(2) INFORMATION FOR SEQ ID NO: 251:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 251:

Cys Thr Arg Pro Ser Asn Asn Thr Arg Lys Ser Ile His Ile Gly Pro
1               5                   10                  15

Gly Arg Ala Phe Tyr Ala Thr Gly Glu Ala Ile Gly Asp Ile Arg Gln
            20                  25                  30

Ala His Cys
        35

(2) INFORMATION FOR SEQ ID NO: 252:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 252:

Cys Ile Arg Pro Ser Asn Asn Thr Arg Lys Ser Ile His Ile Gly Pro
1               5                   10                  15

Gly Arg Ala Phe Tyr Ala Thr Gly Asp Val Ile Gly Asp Ile Arg Gln
            20                  25                  30

Ala His Cys
        35

(2) INFORMATION FOR SEQ ID NO: 253:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 253:

Cys Thr Arg Pro Ser Asn Asn Thr Arg Lys Ser Ile His Ile Gly Ser
1               5                   10                  15

Gly Arg Ala Phe Tyr Ala Thr Gly Glu Val Ile Gly Asp Ile Arg Gln
            20                  25                  30

Ala His Cys
        35

(2) INFORMATION FOR SEQ ID NO: 254:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 254:

Cys Thr Arg Pro Asn Asn Asn Thr Arg Lys Ser Ile His Ile Gly Ser
1               5                   10                  15

Gly Arg Ala Phe Tyr Thr Thr Gly Glu Ile Ile Gly Asp Ile Arg Gln

```
                    20                  25                  30
Ala His Cys
        35

(2) INFORMATION FOR SEQ ID NO: 255:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 255:

Cys Thr Arg Pro Asn Asn Asn Thr Ile Lys Ser Ile His Ile Gly Pro
1               5                  10                  15

Gly Arg Ala Phe Tyr Thr Thr Gly Glu Ile Ile Gly Asp Ile Arg Gln
                20                  25                  30

Ala His Cys
        35

(2) INFORMATION FOR SEQ ID NO: 256:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 256:

Cys Thr Arg Pro Asn Asn Asn Ile Arg Lys Ser Ile His Ile Gly Pro
1               5                  10                  15

Gly Arg Ala Phe Tyr Thr Thr Gly Glu Ile Ile Gly Asp Ile Arg Gln
                20                  25                  30

Ala His Cys
        35

(2) INFORMATION FOR SEQ ID NO: 257:

(i) SEQUENCE CHARACTERISTICS:
        (A) LENGTH: 35 amino acids
        (B) TYPE: amino acid
        (C) STRANDEDNESS: unknown
        (D) TOPOLOGY: circular (ii) MOLECULE TYPE: peptide (iii) HYPOTHETICAL: NO (xi) SEQUENCE DESCRIPTION: SEQ ID NO: 257:

Cys Thr Arg Pro Ser Asn Asn Thr Arg Lys Ser Ile His Ile Gly Pro
1               5                  10                  15

Gly Arg Ala Phe Tyr Ala Thr Gly Glu Val Ile Gly Asp Ile Arg Gln
                20                  25                  30

Ala His Cys
        35
```

NUCLEIC ACIDS AND METHODS FOR THE DISCRIMINATION BETWEEN SYNCYTIUM INDUCING AND NON SYNCYTIUM INDUCING VARIANTS OF THE HUMAN IMMUNODEFICIENCY VIRUS

FIELD OF THE INVENTION

The invention relates to the diagnosis of variants of the human immunodeficiency virus (HIV), in particular of the type 1 virus (HIV-1). The human immunodeficiency virus, which by now may be better defined as a group of related viruses, is the causative agent for the acquired immuno deficiency syndrome, better known as AIDS.

Apart from the variety of viruses which now have been identified as HIV species, there is also a variety within a single virus species, such as HIV-1.

DESCRIPTION OF THE PRIOR ART

HIV-1 phenotype variability plays a keyrole in the pathogenesis of AIDS. In early asymptomatic infection, virus isolates are generally slow replicating, macrophage-tropic and non syncytium inducing (NSI). In the course of infection, isolates with reduced macrophage-tropic capacity and increased replication rates become predominant (M. Tersmette et al. *J. Virol.* 63:2118–2125 1989, H. Schuitemaker et al. *J. Virol.* 65:356–363 1991, H. Schuitemaker et al. *J. Virol.* 66:1354–1360 1992). In 50% of infected individuals, syncytium inducing (SI) variants arise, coinciding with an accelerated depletion of CD4 positive T-lymphocytes and rapid disease progression (M. Koot et al. *Ann. Int. Med.* 118:681–688 1993). In addition, survival time after AIDS diagnosis is reduced for persons with SI isolates (M. Tersmette et al. *Lancet* i:983–985 1989).

Monitoring SI capacity of HIV-1 isolates in seropositive individuals may be used as a prognostic marker for rate of CD4 cell decline and rapid progression to AIDS. The relative risk for disease progression for persons with SI variants is higher than the relative risk of i.e. low CD4 cell numbers or p24 antigenemia and is independent of the latter two markers (M. Koot et al. *Ann. Int. Med.* 118:681–688 1993). Apart from the role of HIV-1 biological variability in the natural course of infection, efficacy of zidovudine treatment appeared to be dependent on the biological phenotype of HIV-1. In a study of zidovudine treated asymptomatic individuals at high risk for progression to AIDS, only transient improvement in CD4 cell numbers and response to anti-CD3 monoclonal antibodies in the zidovudine treated persons was observed. However, zidovudine treatment delayed clinical progression significantly in persons who did not develop SI variants (M. Koot et al. *J. Infect. Dis.* 168:733–736 1993). Therefore, it is important to determine HIV-1 phenotype of participants in anti-viral drug trials for proper randomization to improve evaluation of efficacy of anti-viral therapy.

So far, SI capacity of isolates from seropositive individuals was monitored using either PHA stimulated peripheral blood mononuclear cells (PBMC) or the MT2 T-cell line as indicator. It was shown that the ability to induce syncytia in PHA stimulated PBMC correlated with the ability to replicate in the MT2 T-cell line for all HIV-1 isolates tested (M. Koot et al. *AIDS* 6:49–54 1992). Both methods require specialized laboratory equipment and well trained laboratory personnel since HIV-1 is propagated to high titers. Moreover, the methods require use of purified lymphocytes and are less applicable to whole blood cell samples or serum and plasma samples. In individuals with extremely low CD4 cell numbers (i.e. after AIDS diagnosis) the methods have limited value.

In the search for molecular determinants of HIV-1 SI capacity it was found that the third variable domain (V3) of the envelope molecule gp120 plays an important role in determining SI capacity. Exchange of V3 domains between SI and NSI molecular clones of HIV-1 demonstrated that V3 can confer SI capacity (M. Groenink et al. *Science* 260:1513–1516 1993). Sequence analysis of V3 domains from a set of naturally occurring HIV-1 isolates revealed a nearly 100% correlation between HIV-1 phenotype and aminoacid composition of V3 (R. Fouchier et al. *J. Virol.* 66:3183–3187 1992). In SI HIV-1 isolates the V3 domain harbours positively charged aminoacid residues (Arginine or Lysine) at positions 306 or 320. In NSI HIV-1 isolates both residues are either uncharged or negatively charged. Site directed mutagenesis at these positions in V3 revealed that presence of positively charged residues at either position indeed confers SI capacity (J. De Jong et al. *J. Virol.* 66:757–765 1992).

SUMMARY OF THE INVENTION

The present invention solves the problem of how to make use of these data to discriminate between HIV-1 isolates which do and HIV-1 isolates which do not induce syncytia. The invention provides a method for discriminating between syncytia inducing and non-syncytium inducing variants of the human immunodeficiency virus, wherein the ability to induce syncytium is determined by identifying characterizing nucleotides therefore in either the coding or the non coding strand of the virus. Though the prevalence of the amino acids in HIV-SI variants in comparison with HIV-NSI variants was already known, it was not envisaged how this could be used to discriminate between the two. By Analyzing the difference at the nucleic acid level this discrimination has now become possible in a rapid, easy and safe manner.

In its most general form, the invention described herein presents oligonucleotides with sequences specific for SI HIV-1 isolates that may be used for determination of HIV-1 phenotype in biological materials obtained from seropositive individuals. These oligonucleotides may be variable in length and nucleotide composition, dependent on the technique used for detection, but meet the criteria to discriminate SI from NSI strains based on DNA-sequences responsible for phenotype-specific aminoacid variation at positions 306 and 320 in V3.

In order to determine SI-specific DNA sequence variation first V3 amino acid sequences from 251 isolates obtained from 90 individuals were analyzed for correlation between charge of aminoacid residues at positions 306 and 320 and SI capacity. This correlation was found to be nearly 100% as described earlier (R. Fouchier et al. *J. Virol.* 66:3183–3187 1992) and would therefore allow prediction of viral phenotype. Next, we analyzed the frequency of amino acid substitutions at positions 306 and 320 in V3 from SI and NSI isolates and codon usage at these positions, to investigate the phenotype-restricted DNA sequence variation that encodes phenotype-restricted aminoacid variation. In NSI isolates, a Serine or Glycine residue is present at position 306 in nearly 100% of the virus isolates. In SI isolates, this residue is substituted by an Arginine residue in 48% of the sequences. At position 320 3% of the NSI isolates has a Lysine or Arginine residue whereas in the group of SI viruses 43% has such positively charged residues at this position. Given the relatively restricted aminoacid sequence variation at positions 306 and 320, we emphasized that limited DNA sequence variation could account for differences in SI capacity. Analysis of the DNA sequences that encode the amino acid residues at positions 306 and 320 is shown. Although Arginine residues may be coded for by 6 different codons, presence of Arginine residues at position 306 in V3 results from either an AGG or AGA codon in all SI isolates. In NSI isolates, the last nucleotide of the codon at position 306 is either a T or a C (i.e. AGT and AGC encoding Serine and GGT encoding Glycine for 190 out of 191 NSI isolates). Presence of the Arginine and Lysine residues at position 320 results from codons AAA (Lysine) and AGA (Arginine) in all SI isolates. In 181 out of 191 NSI sequences, either G or C is the first nucleotide in codon 320 (i.e. GAA and GAG encoding Glutamic acid, GAT and GAC encoding aspartic acid, and CAA encoding Glutamine). By using an assay according to the present invention that would allow for discrimination of A and G from C and T residues as the last nucleotide in codon 306 and A from G, C and T residues as the first nucleotide in codon 320, analysis of virus isolates from the 90 individuals in this dataset would have resulted in a proper determination of viral phenotype in 94% of the individuals.

There are a number of ways in which the discrimination between A or G and C or T at codon 306 as well as the discrimination between A and C or G or T at codon 320 can be carried out, a suitable one being described in the experimental part below. Although the invention is explained in detail for the discrimination between SI and NSI variants of HIV-1, it will be clear that a similar discriminative may be found in other HIV species, such as HIV-2. The contribution of this invention to the art, in one part, is the realization that though at the amino acid level a difference may be observable in SI variants as compared to NSI variants, but that this can be exploited to discriminate between the two when applied to the nucleic acid level. This should be broader applicable than for HIV-1 only. On the other hand, it is also a part of the invention how to discriminate between the SI and NSI variants, for which a very elegant method is disclosed in the experimental part.

Usually the methods for discrimination between HIV-SI and HIV-NSI will employ hybridization of an oligonucleotide to either the coding or the non coding strand of the V3 loop of the GP120 protein. These methods will in one way or another make use of the fact that mismatches will occur when hybridizing an oligonucleotide complementary to an SI variant to an NSI variant DNA molecule or vice versa. These hybridization assays are well known in the art and suitable ones such as northern blots, southern blots and in situ hybridization can be selected. They can include, but are not limited to hybridization techniques in which the hybrids are somehow detected, either through attaching a label to the oligonucleotide, or through specific binding reactions between hybrids and reactants provided with a label. In this respect it should be noted that a label is intended to mean any detectable moiety, be it through further reactions, or directly observable in any suitable way.

Suitable hybridization techniques also include the well known amplification techniques, such as NASBA, PCR and the like, in which sets of oligonucleotides (primers) are hybridized to the desired nucleic acid a part of which is to be identified and which serve as a template for an enzyme such as a DNA polymerase which reproduces multiple copies of the part of the nucleic acid of interest. The selectivity of such methods for a large part depends on the selection of suitable primers. The present invention provides novel primers which have been very elegantly chosen to allow for the discrimination between SI and NSI variants. It is often sufficient to use just one of the novel specific primers according to the invention, as disclosed in the experimental part, with one of the primers complementary to a more conserved region, but many suitable combinations can be designed by the man skilled in the art without departing from the spirit of the present invention. For instance a sequence at least 70% homologous with, a primer according to the invention or a sequence which hybridizes to such a sequence or its complementary counterpart under stringent conditions can be used. The invention will now, for illustration purposes only, be explained in more detail in the following experimental part.

EXPERIMENTAL

Figure 3:
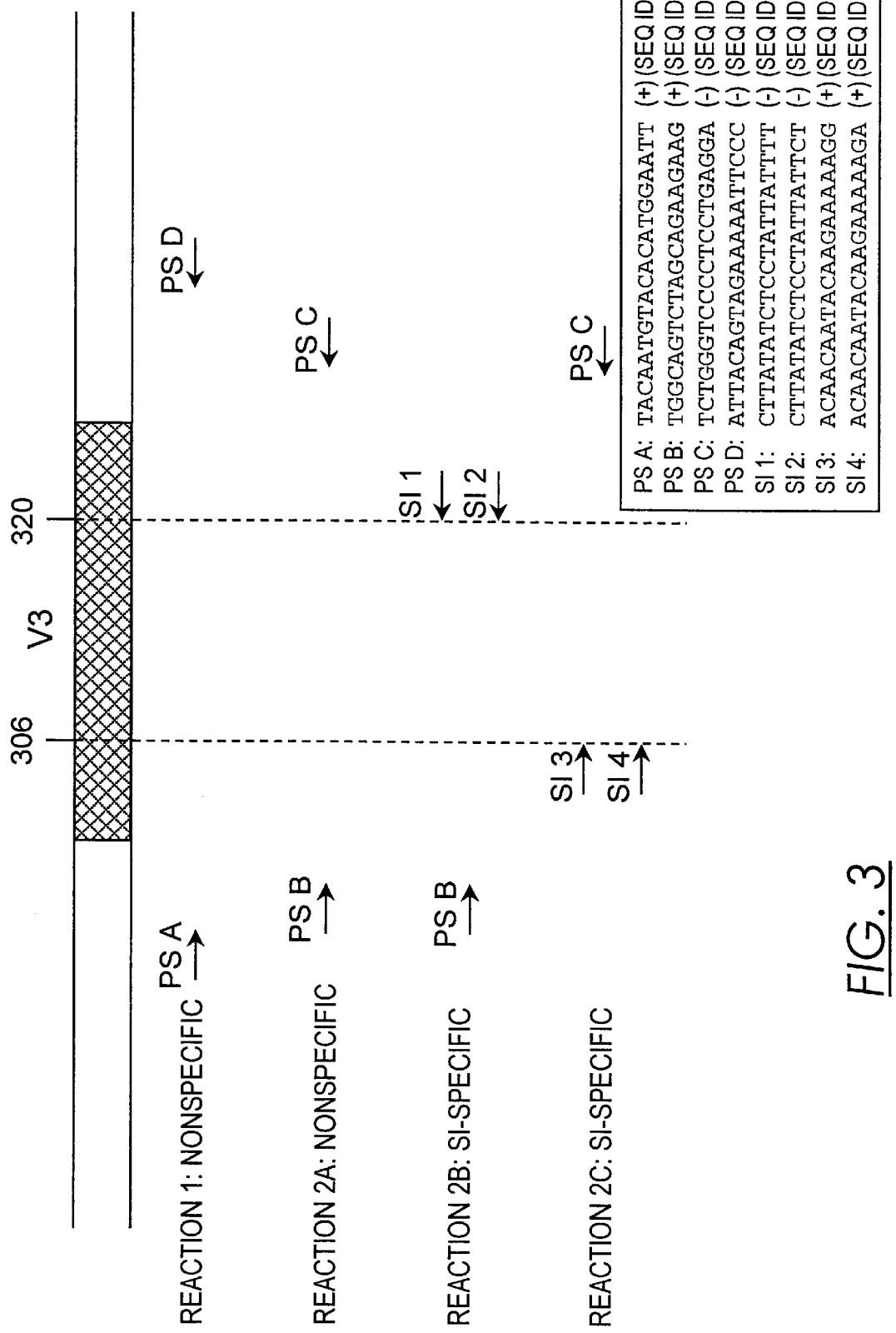

The limited phenotype-restricted DNA sequence variation at positions 306 and 320 was used to design phenotype-specific oligonucleotides (primers) for selective amplification of SI V3 sequences by PCR (FIG. 3). 2 oligonucleotide primers spanning position 306 in V3 were synthesized, that had either a G or A at the ultimate 3' position. Since all NSI isolates harbour either T or C at this position and mismatches at the extreme 3' end of PCR primers hamper PCR amplification, use of these primers would not allow amplification of NSI V3 sequences by PCR. Similarly, 2 oligonucleotide primers spanning position 320 in V3 were designed oligonucleotides for selective amplification of SI isolates that have an Arginine or Lysine residue at position 320 should anneal to either AA or AG at the ultimate 3' position. All 4 20-mer oligonucleotides are designed to have full similarity to the B-type consensus V3 DNA sequence next to these SI-specific substitutions at the 3' ends. The 4 SI-specific primers were used in combination with previously described oligonucleotides as outlined in FIG. 3. To ensure sensitivity we used a nested PCR with primers PS A and PS D in the first reaction and combinations of primers PS B, PS C and SI 1 to 4 as shown in FIG. 3 in the second. Primers PS A to D recognize relatively conserved sequences outside V3, to ensure annealing to both SI and NSI V3 sequences. Parts of this first reaction were subjected to amplification with primersets PS B-PS C, PS B-SI 1+2 and PS C-SI 3+4. Set PS B-PS C would allow amplification of V3 from both SI and NSI isolates and were therefore used as positive control, whereas sets PS B-SI 1+2 and PS C-SI 3+4 would selectively amplify V3 from viruses with basic residues at positions 320 and 306 respectively. For practical reasons, 2 combinations of 2 SI-specific oligonucleotides were used rather than 4 reactions with I SI-specific oligonucleotide. Because of the 95% homology between each 2 oligonucleotides, annealing temperatures were expected to be rather comparable which would ensure efficient amplification with both primers in one reaction.

Figure 4:
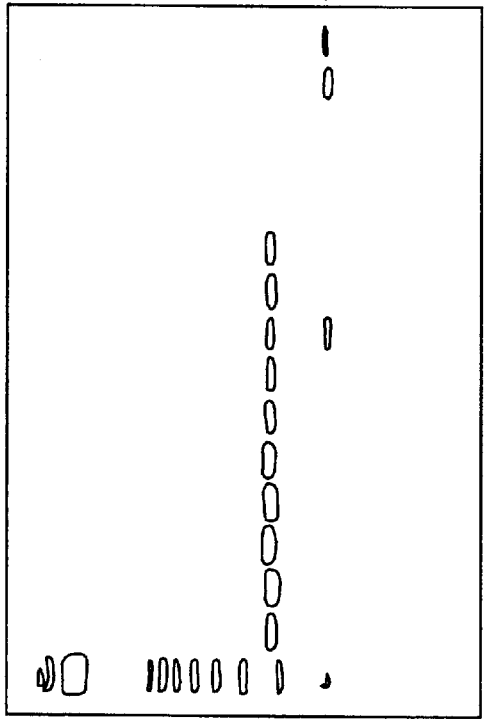

To optimize PCR annealing temperatures for SI-specific primersets we used a set of 5 virus isolates of which 4 had V3 sequences that perfectly matched either 1 of the 4 SI specific oligonucleotides (FIG. 4, upper panel). ACH-320.2a.5 and ACH-479.7 are recognized by PS B in combination with SI 1 and 2 respectively, ACH168.7 and HIV-IIIb are recognized by PS C in combination with SI 3 and 4 respectively. Isolate ACH-172.Ba-L displayed complete similarity to the V3 consensus DNA sequence around positions 306 and 320 and should therefore not be amplified with any of the 4 oligonucleotides. In the lower panel of FIG. 4, results of PCR amplification with the 3 primersets are shown. Primerset PS B-SI 1+2 allowed amplification of V3 from ACH-320.2a.5 and ACH-479.7 but not the other 3 isolates at 48° C. Annealing at lower temperatures resulted in amplification of V3 from ACH172.Ba-L. Primerset PS C-SI 3+4 allowed amplification of V3 from ACH-168.7 and HIV-IIIb but not the other 3 isolates at 54° C. Annealing-temperatures of 52° C. and lower resulted in amplification of V3 sequences with mismatches at the 3' end of primers SI 3 and 4. Primorset PS B-PS C allowed amplification of V3 from all 5 isolates within the range of annealing-temperatures tested (37° C. to 58° C.). For further experiments, annealing temperature for primersets PS B-PS C and PS B-SI 1+2 was 48° C., for primerset PS-C-Si 3+4 54° C.

Figure 5:
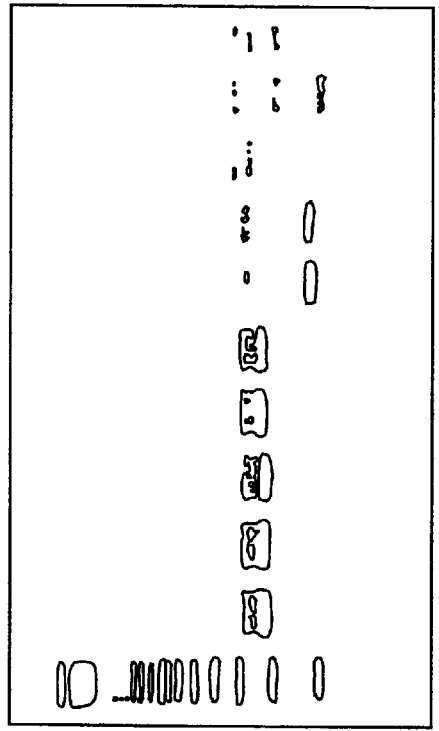

Since in naturally occurring HIV-1 isolates V3 sequences may be highly heterogeneous (see i.e. FIG. 2, right column), we next determined whether mutations at positions flanking the 3' ends in the 20-mer oligonucleotide annealing-site were allowed for PCR amplification. In the set of isolates shown in FIG. 2, the maximum number of mutations in the primer annealing-site for SI isolates with basic residues at position 320 was 2. For SI isolates with basic residues at position 306 the number of mutations was 3 or less, with the exception of isolates from 1 individual (Ams164) that had up to 7 mutations. The results of PCR amplification of V3 from these SI isolates are shown in FIG. 5, together with DNA-sequences of the primer recognition sites. It can be seen from FIG. 5 that up to 3 mutations in the regions recognized by the oligonucleotides did not result in negative PCR signals. For isolates with 6 mutations in the SI 3+4 oligonucleotide annealing site, PCR would not allow amplification of V3. Fortunately, the number of isolates with such high diversity from the oligonucleotide-sequence was found to be extremely low (FIG. 2).

Our PCR-based assay thus allows discrimination of SI and NSI isolates with this set of oligonucleotides. It is obvious that by using other techniques, these oligonucleotides or oligonucleotides with sequences based on the here defined SI-specific nucleotide substitutions would allow discrimination of SI and NSI HIV-1 isolates. The oligonucleotides for such assays for detection of SI HIV-1 isolates may be variable in length and/or nucleotide composition but have the SI-specific residues described herein in common. It will be clear to the man skilled in the art that it is possible to selectively amplify the sequence between codons 306 and 320 as well as sequences upstream from codon 306 end downstream from codon 320, as long as the last nucleotide at the ultimate 3' end of one of the primers is discriminative for the occurrence of amplification, meaning that it results in a mismatch for one variant and thus giving no amplified material and resulting in a match and thus amplification for the other variant. These and similar variations based on the present invention as disclosed herein above will be readily available for the man skilled in the art without departing from the present invention.

What is claimed is:

1. An isolated and purified oligonucleotide primer having a length of 11 to 20 nucleotides, which is capable of detecting human immunodeficiency virus type 1 (HIV-1) syncytium-inducing (SI) or non-syncytium inducing (NSI) variants and comprising a nucleotide sequence at its 3' end selected from the group consisting of SEQ ID NO:1, SEQ ID NO:2, SEQ ID NO:3 and SEQ ID NO:4.

2. The oligonucleotide primer of claim 1, wherein the primer is selected from the group consisting of SEQ ID NO:5, SEQ ID NO:6, SEQ ID NO.7 and SEQ ID NO:8.

3. A method for discriminating between syncytium inducing (SI) or non-syncytium inducing (NSI) human immunodeficiency virus type 1 (HIV-1) isolates by detecting genotypic differences at the triplet codon for amino acid position 320 of the V3 loop of the envelope glycoprotein gp120 comprising the following:

(a) obtaining and preparing a sample comprising viral genomic RNA, the non-coding or coding strand of viral cDNA, or the coding or non-coding strand of a proviral genome;

(b) performing an amplification reaction on said sample with a first primer derived from a conserved region located upstream of the V3 loop and one or more second primers containing a nucleotide sequence at the 3' end thereof selected from the group consisting of SEQ ID NO:1 and SEQ ID NO:2; and (c) determining whether an amplification product was obtained in step (b), wherein the presence of amplified product indicates the presence of an HIV-1 SI variant.

4. The method of claim 3, wherein said first primer has the sequence of SEQ ID NO:19.

5. The method of claim 3, wherein the amplification step (b) includes two of said second primers containing in one second primer a nucleotide sequence at the 3' end thereof according to SEQ ID NO:1 and in the other second primer a nucleotide sequence at the 3' end thereof according to SEQ ID NO:2.

6. A method for discriminating between syncytium inducing (SI) or non-syncytium inducing (NSI) human immunodeficiency virus type 1 (HIV-1) isolates by detecting genotypic differences at the triplet code for amino acid position 306 of the V3 loop of the envelope glycoprotein gp120 comprising the following:

(a) obtaining and preparing a sample comprising viral genomic RNA, the non-coding or coding strand of viral cDNA, or the coding or non-coding strand of a proviral genome;

(b) performing an amplification re action on said sample with one or more first primers containing a nuclotide sequence at the 3' end thereof selected from the group consisting of SEQ ID NO:3 and SEQ ID NO:4, and a second primer derived from a conserved region located downstream of the V3 loop; and (c) determining whether an amplification product was obtained in step (b), wherein the presence of amplified product indicates the presence of an HIV-1 SI variant.

7. The method of claim 6, wherein said second primer has the sequence of SEQ ID NO:20.

8. The method of claim 6, wherein the amplification step (b) includes two of said first primers containing in one first primer a nucleotide sequence at the 3' end thereof according to SEQ ID NO:3 and in the other first primer a nucleotide sequence at the 3' end thereof according to SEQ ID NO:4.

* * * * *